United States Patent
Chang et al.

(10) Patent No.: US 11,976,314 B2
(45) Date of Patent: May 7, 2024

(54) METHOD FOR CONVERTING NON-ETHANOL PRODUCING, ACETOGENIC STRAIN TO ETHANOL-PRODUCING STRAIN AND METHOD FOR PRODUCING ETHANOL FROM SAME ETHANOL-PRODUCING STRAIN BY USING CARBON MONOXIDE

(71) Applicants: GWANGJU INSTITUTE OF SCIENCE AND TECHNOLOGY, Gwangju (KR); KOREA UNIVERSITY RESEARCH AND BUSINESS FOUNDATION, Seoul (KR)

(72) Inventors: In Seop Chang, Gwangju (KR); Jiyeong Jeong, Gwangju (KR); Shinyoung Park, Gwangju (KR); In-Geol Choi, Seoul (KR); Byeonghyeok Park, Seoul (KR)

(73) Assignees: GWANGJU INSTITUTE OF SCIENCE AND TECHNOLOGY, Gwangju (KR); KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 1102 days.

(21) Appl. No.: 16/643,126

(22) PCT Filed: Aug. 28, 2018

(86) PCT No.: PCT/KR2018/009923
§ 371 (c)(1),
(2) Date: Jun. 3, 2020

(87) PCT Pub. No.: WO2019/045416
PCT Pub. Date: Mar. 7, 2019

(65) Prior Publication Data
US 2023/0193325 A1 Jun. 22, 2023

(30) Foreign Application Priority Data
Aug. 29, 2017 (KR) .......................... 10-2017-0109483

(51) Int. Cl.
C12P 7/08 (2006.01)
C12N 1/21 (2006.01)
C12N 9/04 (2006.01)
C12N 15/74 (2006.01)

(52) U.S. Cl.
CPC .............. *C12P 7/08* (2013.01); *C12N 9/0006* (2013.01); *C12N 15/74* (2013.01); *C12Y 101/01001* (2013.01)

(58) Field of Classification Search
None
See application file for complete search history.

(56) References Cited

U.S. PATENT DOCUMENTS

2011/0236941 A1* 9/2011 Koepke ................ C12N 9/0008
435/160
2017/0327849 A1* 11/2017 Liew .............. C12Y 102/07005

FOREIGN PATENT DOCUMENTS

| KR | 101076042 B | 10/2011 |
| KR | 1020130079599 A | 7/2013 |
| WO | WO2009094485 A1 | 7/2009 |

OTHER PUBLICATIONS

Roh et al., Complete Genome Sequence of a Carbon Monoxide-Utilizing Acetogen, Eubacterium limosum KIST612, J. Bacteriol. 193, 2011, 307-08. (Year: 2011).*
Kang et al., Metabolism perturbation Caused by the overexpression of carbon monoxide dehydrogenase/Acetyl-CoA synthase gene complex accelerated gas to acetate conversion rate of Eubacterium limosum KIST612, Biotechnol. Res. 341, 2021, 125879. (Year: 2021).*
Genank, Accession No. CP0011914, 2016, www.ncbi.nlm.gov. (Year: 2016).*
Shin et al., Genome Engineering of Eubacterium limosum Using Expanded Genetic Tools and the CRISPR-Cas9 System, ACS Synth. Biol. 8, 2019, 2059-68. (Year: 2019).*
GenBank, Accession No. MP540140.1, 2020, www.ncbi.nlm.nih.gov. (Year: 2020).*
Chang, I., et al., "Isolation and Identification of Carbon Monoxide Utilizing Anaerobe, Eubacterium Limosum KIST612", "Kor. J. Appl. Microbiol. Biotechnol,", 1997, pp. 1-8, vol. 25, No. 1.
Chang, I., et al., "CO Fermentation of Eubacterium Limosum KIST612", "J. Microbiol. Biotechnol.", 1998, pp. 134-140, vol. 8, No. 2.
Chang, I., et al., "Formulation of Defined Media for Carbon Monoxide Fermentation by Eubacterium Limosum KIST612 and the Growth Characteristics of the Bacterium", "Journal of Bioscience and Bioengineering", 1999, pp. 682-685, vol. 88, No. 6.
Chang, I.S., et al., "Heterologous Gene Expression Enables Sole Production of Non-Native Ethanol by Acetogen, Eubacterium Limosum KIST612", "SIMB Annual Meeting and Exhibition", Aug. 12, 2018, p. 27.
Drake, H., et al., "Old Acetogens, New Light", "Annals oof the New York Academy of Sciences", 2008, pp. 100-128, vol. 1125.
Genbank, "Eubacterium Limosum Strain ATCC 8486 Chromosome, Complete Genome", "GenBank CP019962", Apr. 6, 2017, pp. 1-3.
Genbank, "Eubacterium Limosum Strain SA11, Complete Genome", "GenBank CP011914", Mar. 17, 2016, pp. 1-621.

(Continued)

*Primary Examiner* — Todd M Epstein
(74) *Attorney, Agent, or Firm* — HULTQUIST, PLLC; Steven J. Hultquist

(57) ABSTRACT

The present invention relates to a transformed strain having ethanol production potential, constructed by introducing a foreign gene for ethanol production into a non-ethanol producing acetogen *Eubacterium limosum* and a method for producing ethanol, using the strain. According to the present invention, *Eubacterium limosum* which is a conventional acetogen lacking ethanol production potential is used to produce ethanol, which is a high value-added product, as a single product from carbon monoxide contained in waste gas.

7 Claims, 6 Drawing Sheets

Specification includes a Sequence Listing.

(56) References Cited

OTHER PUBLICATIONS

Genbank, "Shuttle Vector pJIR1457, Complete Sequence", "GENBANKU9055.1", 2003, pp. 1-3.

Kletzin, A., et al., "Molecular Characterization of the Genes Encoding the Tungsten-Containing Aldehyde Ferredoxin Oxidoreductase from Pyrococcus Furiousus and Formaldehyde Ferredoxin Oxidoreductase from Thermococcus Litoralis", "Journal of Bacteriology", Aug. 1995, pp. 4817-4819, vol. 177, No. 16.

Liew, F., et al., "Metabolic Engineering of Clostridium Autoethanogenum for Selective Alcohol Production", "Metabolic Engineering", Mar. 2017, pp. 104-114, vol. 40.

Schiel-Bengelsdorf, B., et al., "Pathway Engineering and Synthetic Biology Using Acetogens", "FEBS Letters", 2012, pp. 2191-2198, vol. 586.

Sloan, J., et al., "Construction of a Sequenced Clostridium Perfringens—*Escherichia coli* Shuttle Plasmid", "Plasmid", 1992, pp. 207-219, vol. 27.

Kim, J., et al., "Genome-Based Reclassification of Strain KIST612, Previously Classified as Eubacterium limosum, into a New Strain of Eubacterium callanderi", J. Microbiol. Biotechnol. 2023. 33(8): 1084-1090; https://doi.org/10.4014/jmb.2304.04011.

\* cited by examiner ions with a high-expression promoter, and have found that the transformed strain produced ethanol through a carbon monoxide substrate-specific pathway, thereby completing the present invention.

METHOD FOR CONVERTING NON-ETHANOL PRODUCING, ACETOGENIC STRAIN TO ETHANOL-PRODUCING STRAIN AND METHOD FOR PRODUCING ETHANOL FROM SAME ETHANOL-PRODUCING STRAIN BY USING CARBON MONOXIDE

CROSS-REFERENCE TO RELATED APPLICATIONS

This application is a U.S. national phase under the provisions of 35 U.S.C. § 371 of International Patent Application No. PCT/KR18/09923 filed Aug. 28, 2018, which in turn claims priority under 35 U.S.C. § 119 of Korean Patent Application No. 10-2017-0109483 filed Aug. 29, 2017. The disclosures of International Patent Application No. PCT/KR18/09923 and Korean Patent Application No. 10-2017-0109483 are hereby incorporated herein by reference in their respective entireties, for all purposes.

REFERENCE TO SEQUENCE LISTING

This application includes an electronically submitted sequence listing in .txt format. The .txt file contains a sequence listing entitled "509 SeqID ST25.txt" created on Feb. 28, 2020 and is 31,588 bytes in size. The sequence listing contained in this .txt file is part of the specification and is hereby incorporated by reference herein in its entirety.

TECHNICAL FIELD

The present invention relates to a transformed strain having ethanol-producing ability, produced by introducing a gene for ethanol production into an acetogen having no ethanol-producing ability, *Eubacterium limosum*, and a method for producing ethanol from carbon monoxide using the strain.

BACKGROUND ART

Recent emerging carbon upcycling technologies produce resources using, as raw materials, carbon monoxide, carbon dioxide, methane, natural gas or the like produced from fossil fuels, and are in the spotlight as a new industrial innovation owing to effects such as greenhouse gas reduction and energy self-sufficiency.

Waste gas (synthetic gas) refers to a mixed gas consisting of carbon monoxide (CO), carbon dioxide ($CO_2$), and hydrogen ($H_2$) obtained through gasification of various carbon-based raw materials such as waste, coal, coke, lower hydrocarbon gas, naphtha and heavy oil. Microorganisms that produce acetate through anaerobic metabolism using synthetic gas or sugar as carbon and energy sources are called "Acetogens" which are capable of producing not only acetate, a main product using waste gas as carbon and energy sources, but also an organic acid such as a butyric acid and a bio-alcohol such as ethanol or butanol (HL Drake et al., *Annals of the New York Academy of Sciences*, 1125:100, 2008).

At present, international companies such as Coskata, INEOS Bio and Lanza Tech have already industrially produced bio-fuels using acetogenic strains. Accordingly, the importance of research aimed at the independent development and improvement of strains free from restrictions on use thereof due to patents is emphasized in Korea (B Schiel-Bengelsdorf et al., *FEBS Letters*, 586(15):219, 2012).

More than about 100 acetogenic bacteria are known at present, but only a few strains produce 4-carbon organics such as butyric acid by consuming waste gas. In addition, there is only a few case that metabolic engineering approach targeting specific acetogenic bacteria for increasing metabolite productivity has been successfully realized and commercialized due to considerable difficulty in establishing a genetic engineering system suitable for acetogens, which are gram-positive strict anaerobic strains.

Accordingly, as a result of extensive efforts to develop an acetogenic strain capable of producing ethanol from a synthetic gas containing carbon monoxide, the present inventors have produced a transformed strain by introducing a foreign aldehyde alcohol dehydrogenase gene into a *Eubacterium limosum* KCTC13263BP strain, which has excellent carbon monoxide availability and production efficiency, but does not produce ethanol, to regulate the expression with a high-expression promoter, and have found that the transformed strain produced ethanol through a carbon monoxide substrate-specific pathway, thereby completing the present invention.

DISCLOSURE

Technical Problem

It is an object of the present invention to provide a transformed acetogenic strain having ethanol-producing ability, produced by introducing a gene encoding a bifunctional aldehyde alcohol dehydrogenase into an acetogen having no ethanol-producing ability.

It is another object of the present invention to provide a method of preparing ethanol by culturing the transformed acetogenic strain.

It is still another object of the present invention to provide a vector for expressing a *Eubacterium limosum* strain comprising a constitutive strong promoter derived from *Eubacterium limosum*.

Technical Solution

To achieve the above objects, the present invention provides a transformed *Eubacterium limosum* strain having ethanol-producing ability, in which a gene encoding a bifunctional aldehyde alcohol dehydrogenase is introduced into *Eubacterium limosum* having no ethanol-producing ability.

The present invention also provides a method of preparing ethanol comprising: (a) culturing the transformed *Eubacterium limosum* strain in the presence of a carbon monoxide-containing gas to produce ethanol; and (b) recovering the produced ethanol.

The present invention also provides a *Eubacterium limosum*-derived promoter having a nucleotide sequence represented by SEQ ID NO: 2 and a vector for expressing the *Eubacterium limosum* strain having a nucleotide sequence represented by SEQ ID NO: 1.

DETAILED DESCRIPTION AND EXEMPLARY EMBODIMENTS

Figure 1:
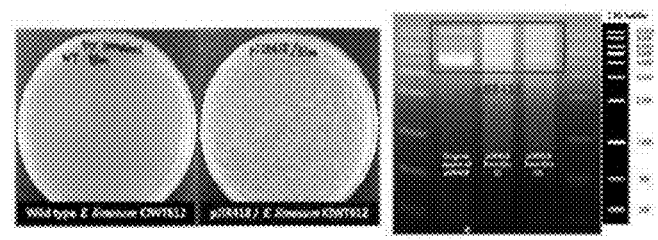
FIG. 1 shows a process of producing a shuttle vector backbone having a reduced size for a *Eubacterium limosum* KCTC13263BP strain by recombining the major region sequence of a pJIR418 vector.
Figure 1:
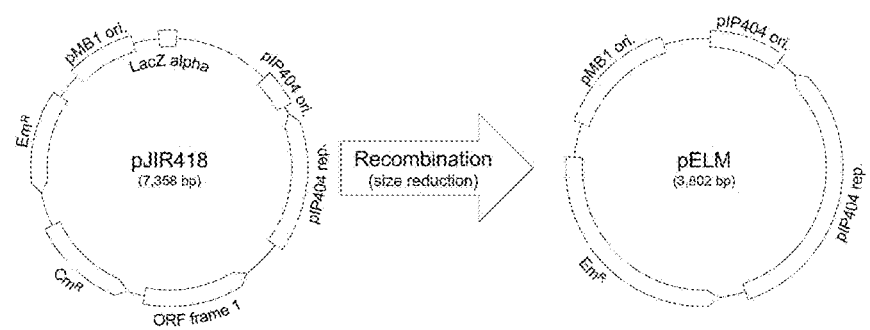

In the present invention, metabolic engineering was performed to produce value-added ethanol from carbon monoxide using *Eubacterium limosum* KCTC13263BP, which is an acetogen producing no ethanol, and the fact that genes expressing aldehyde ferredoxin oxidoreductase (AOR) serving as an enzyme which catalyzes conversion from acetate to acetaldehyde are present on the genome of the strain, supported the notion that the ethanol-producing transformed strain, to which the metabolic engineering is applied, produces ethanol in an energy-efficient manner by reusing the produced acetate through the AOR, while maintaining an acetate production pathway, which is a major energy production pathway of acetogen. The ethanol production pathway through reusing acetate produces ethanol by reusing a reduced ferredoxin ($Fd^{2-}$) as a motive force while retaining ATP obtained through substrate-level phosphorylation during initial acetate production. For this reason, ATP can be maintained and thus energy loss can be minimized compared to a metabolic pathway that produces ethanol through acetaldehyde directly from acetyl-CoA. A strain capable of producing ethanol from a carbon monoxide substrate in an energy-efficient manner through metabolic engineering can improve ethanol production to an industrially applicable level when ultimately applied to a reactor optimized for substrate transfer and product separation.

The *E. limosum* strain used as an acetogen in one aspect of the present invention is a strain that has high resistance to carbon monoxide, actively grows from carbon monoxide as a sole carbon source, and produces useful organic acids such as acetic acid and butyric acid (Chang I S et al., *J. Microbiol. Biotechnol.*, 8:134, 1998; Jang In-seop, *Kor. J. Appl. Microbiol. Biotechnol.*, 25:1, 1997). In addition, three genes (ELI_0332, ELI_1752, ELI_3389) expressing an aldehyde ferredoxin oxidoreductase (AOR), the reversible enzyme that catalyzes the conversion of carboxylic acid such as acetic acid to aldehyde such as acetaldehyde, are present in the genome of the wild-type strain. Among them, ELI_1752 has very high homology with the major conserved bases and motifs on the amino acid sequence of AOR of the *Pyrococcus furiosus* strain in which the catalytic function of AOR was first found. This suggests that the AOR of the strain also perform the same function as the previously known AOR (Kletzin A et al., *J Bacteriol.*, 177(16):4817-9, 1995).

In one aspect of the present invention, first, an introduction of foreign gene and expression system suitable for an acetogen, *E. limosum* strain are established, and based on the same, a gene encoding a bifunctional aldehyde alcohol dehydrogenase is introduced into the wild-type strain to produce a transformed strain having ethanol-producing ability.

Thus, in one aspect, the present invention is directed to a transformed *Eubacterium limosum* strain having ethanol-producing ability, in which a gene encoding a bifunctional aldehyde alcohol dehydrogenase is introduced into *Eubacterium limosum* having no ethanol-producing ability.

In the present invention, the bifunctional aldehyde alcohol dehydrogenases selected and used herein are AdhE1 and AdhE2 derived from *Clostridium autoethanogenum*, which have high homology of 85% or more with AdhE1 and AdhE2 of ethanol-producing strains such as *C. ljungdahlii* and *C. carboxidivorans*.

In one aspect of the present invention, in order to select a promoter having a constant high-expression efficiency (strong constitutive promoter) for the *E. limosum* strain, a transcript expression average of each of a total of 4,579 genes on the genome is determined based on the result of analysis of transcripts obtained during the exponential growth phase of the strain under various culture conditions. The promoters of the upstream of genes having high transcript expression values are selected and respective insertion genes linked to β-glucuronidase (GUS)-expressing genes using the promoters are constructed. The insertion genes are linked to a shuttle vector and an expression vector for *E. limosum* to perform cloning, and a promoter with high GUS activity is identified and used as an autologous constitutive strong promoter for the *E. limosum* strain.

Thus, transcription of the gene encoding the bifunctional aldehyde alcohol dehydrogenase is regulated by a promoter represented by the nucleotide sequence of SEQ ID NO: 2.

In the present invention, *Eubacterium limosum* may be a *Eubacterium limosum* KCTC13263BP strain.

In the present invention, the introduction of the foreign gene into the *E. limosum* strain may be carried out using a shuttle vector pELM represented by the nucleotide sequence of SEQ ID NO: 1.

In another aspect, the present invention is directed to a method of preparing ethanol comprising: (a) culturing the transformed *Eubacterium limosum* strain in the presence of a carbon monoxide-containing gas to produce ethanol; and (b) recovering the produced ethanol.

The transformed *E. limosum* strain of the present invention is found to be capable of converting acetaldehyde to ethanol by directly reusing acetate, which is an inherent primary metabolite of a wild-type strain, under autotrophic CO substrate conditions, and to be capable of producing only ethanol without producing butyrate as another metabolite.

The transformed *E. limosum* strain of the present invention was proved to produce only ethanol in a significant concentration of about 28 mM without an additional metabolite by consuming 11.5 mmol (millimoles) of carbon monoxide without the manipulation of genomic DNA under autotrophic substrate conditions, rather than heterotrophic substrate conditions. The transformed strain containing AdhE1 obtained by the present invention is expected to act as a very promising biocatalyst in terms of industrial applicability when applied to a synthetic gas process in the future, since a product separation step in the downstream of the synthetic gas process can be omitted or simplified.

In addition, the present invention suggests an optimal ethanol production pathway in terms of energy acquisition efficiency under carbon monoxide substrate conditions and identifies that the transformed strain produces only ethanol as a single product without other competing metabolites through an optimal pathway and is thus industrially invaluable.

In one aspect of the present invention, in order to produce a shuttle vector suitable for the introduction of a foreign gene into the *E. limosum* strain, a shuttle vector pELM for the *E. limosum* strain represented by the nucleotide sequence of SEQ ID NO: 1 and having a reduced size was produced by using the pJIR418 vector (Sloan J et al., *Elsevier*, 27:3, 1992) found to be stably replicated when conventionally introduced into the *E. limosum* strain, by recombining only the major gene parts on the pJIR412 vector, such as antibiotic resistance cassettes, Gram-negative replication initiation points and Gram-positive replication initiation points.

The vector for foreign gene expression may comprise the constitutive strong promoter for the strain represented by a nucleotide sequence of SEQ ID NO: 2 and a vector backbone represented by the nucleotide sequence of SEQ ID NO: 1.

Hereinafter, the present invention will be described in more detail with reference to examples. However, it will be obvious to those skilled in the art that these examples are provided only for illustration of the present invention and should not be construed as limiting the scope of the present invention.

Example 1: Establishment of Transformation Method Customized for *Eubacterium limosum* KCTC13263BP Strain and Production of Shuttle Vector Electroporation was used as a transformation method for introducing foreign genes into the *Eubacterium limosum* KCTC13263BP strain (hereinafter referred to as "Elm strain") and a slightly modified version of the method used by Ching Leang et al. (*Appl Environ Microbiol.*, 79: 1102, 2013) was used.

For the transformation through electroporation, an electrocompetent cell of the Elm strain was prepared through the following procedure. The Elm strain was precultured to $OD_{600}$ of 1 in 100 ml of HEPES-buffer base medium containing 20 mM glucose (medium, in which, in the composition of a phosphate buffer base medium, disclosed in Chang I S et al., *J Biosci Bioeng.*, 88:682, 1999, the phosphate buffer was changed to 20 mM HEPES buffer; HBBM-Glc), and the culture medium was inoculated in 500 ml of a HBBM-Glc medium supplemented with 20 mM DL-threonine and having the same composition as above to perform main culture. The Elm strain cultured to $OD_{600}$ of 0.7 to 0.8 was washed twice with SMP buffer (containing 270 mM sucrose, 1 mM $MgCl_2$, 7 mM sodium phosphate, 3.17 mM L-cysteine hydrochloride, pH 7.4), resuspended in the final 5 ml of SMP buffer, and concentrated to 100 times or more to prepare the electrocompetent cell of the Elm strain.

2 ng of the vector DNA to be introduced was added to 500 μl of the prepared electrocompetent cell of the Elm strain, and a pulse was applied to the resulting mixture at 3 kV/cm, 400Ω and 25 μF to perform electroporation. The pulsed mixture of the electrocompetent cell and the vector was inoculated in 5 ml HBBM-Glc and cultured overnight. Elm strain transformants were inoculated at 3% in a HBBM-Glc liquid culture medium containing an antibiotic specific for the selection marker located in the vector, or were seeded on a solid agar plate and then selected.

In order to produce gene vectors for stable introduction and expression of foreign genes into the Elm strain, a shuttle vector pELM (SEQ ID NO: 1) having a reduced size for the Elm strain was produced by using the pJIR418 vector (Sloan J et al., *Elsevier*, 27: 3, 1992) found to be stably replicated when introduced into the Elm strain by recombining only the major gene parts on the pJIR412 vector, such as antibiotic resistance cassettes, Gram-negative replication initiation points and Gram-positive replication initiation points (FIG. 1).

Example 2: Screening of Autologous Promoter of
Eubacterium limosum KCTC13263BP Strain for
High Expression of Ethanol-Producing Enzyme In this embodiment, in order to increase the expression efficiency of the foreign genes in the Elm strain, the promoters of genes constantly exhibiting a high expression rate in the Elm strain were screened to select constitutive strong promoters.

Figure 2:
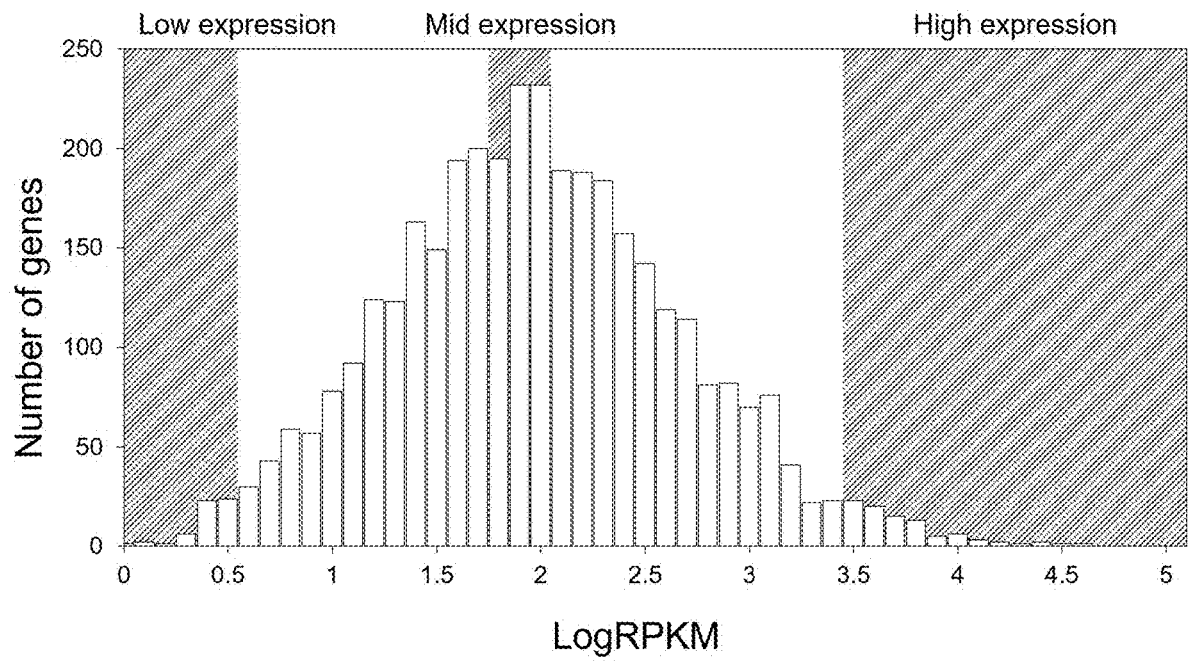
FIG. 2 is a histogram graphed using the average value of transcript expression of each of genes on the entire genome of a total of 3,611 strains based on the result of analysis of a transcript obtained during exponential growth stage of the *Eubacterium limosum* KCTC13263BP strain under three culture conditions, wherein genes having high/middle/low transcript expression values are represented in respective sections.

First, transcript analysis was performed for each substrate to determine the expression level of each of 4,579 genes in the genome of the Elm strain. The Elm strain was separately cultured under four types of substrate conditions (glucose, CO, $CO/CO_2$, $H_2/CO_2$) and in two growth stages (mid-log phase, early-stationary) under each substrate condition. As a result, transcript analysis was performed by sampling the culture solution in triplicate under eight different environmental conditions, RPKM (Reads Per Kilobase of transcript per Million mapped reads) of 4,579 genes annotated in the Elm strain under the eight conditions were finally obtained, an average of RPKM values of respective genes was obtained under eight environmental conditions, and a histogram was created from the average to obtain a normal distribution graph (FIG. 2).

Two genes (ELI_4394, ELI_3815) were finally selected as gene candidates having a constitutive strong promoter from the top 3% of genes having a high RPKM average by determining whether or not the standard deviation of RPKM value under each substrate and growth condition is low, and the sequence of the upstream of 100 bp in the start codon of the corresponding gene does not overlap the ORF of the previous gene based on the normal distribution graph, and the predicted promoter sections of the upstream of the ORF of the two genes were referred to as "promoter H1" (SEQ ID NO: 3) and "promoter H2" (SEQ ID NO: 2). As control groups for the two genes (ELI_4394 and ELI_3815) having a high average expression value, a gene having a middle expression value (ELI_0016) and a gene having a low expression value (ELI_1842) were also selected based on the criteria described above, and predicted upstream promoter sections thereof were referred to as "promoter M1" (SEQ ID NO: 4) and "promoter L1" (SEQ ID NO: 5), respectively.

Promoter H1
(SEQ ID NO: 3)
TTTTTTTATGTAAAAAAGTTAGTTAAAAATAACAAAATTAATGATAATCA

AAGAAAAAGTGGGTATAATTAAAGATAGCGAAATAGGAAACCAATACAGG

AGGAAAAAGA

Promoter H2
(SEQ ID NO: 2)
TTTTCCGTTTAAAGTTTAAAAATTGTGGTATAATTAATTATATCATTAAG

CGGATAAGTGGGTTACACGGACTGCTCAAAATTATATTTGGACTATAGGA

GGTCTTTATT

Promoter M1
(SEQ ID NO: 4)
GCTTTTGCCTATCTTTTTAATTATATAATACTATTTGCCAAACTCATTCC

ACTAAAGTACAATAGAATCATCAAATCTCACACAAAGGATTTTTAT

Promoter L1
(SEQ ID NO: 5)
GTATTTGGATGGGGATCTTCCTTGACGCTTTAAGGGGACTCCGATATGAT

GAAATCAACCAAACAGACAAATCTCAAGATTAAGAAGGAGACACATATTC

Figure 3:
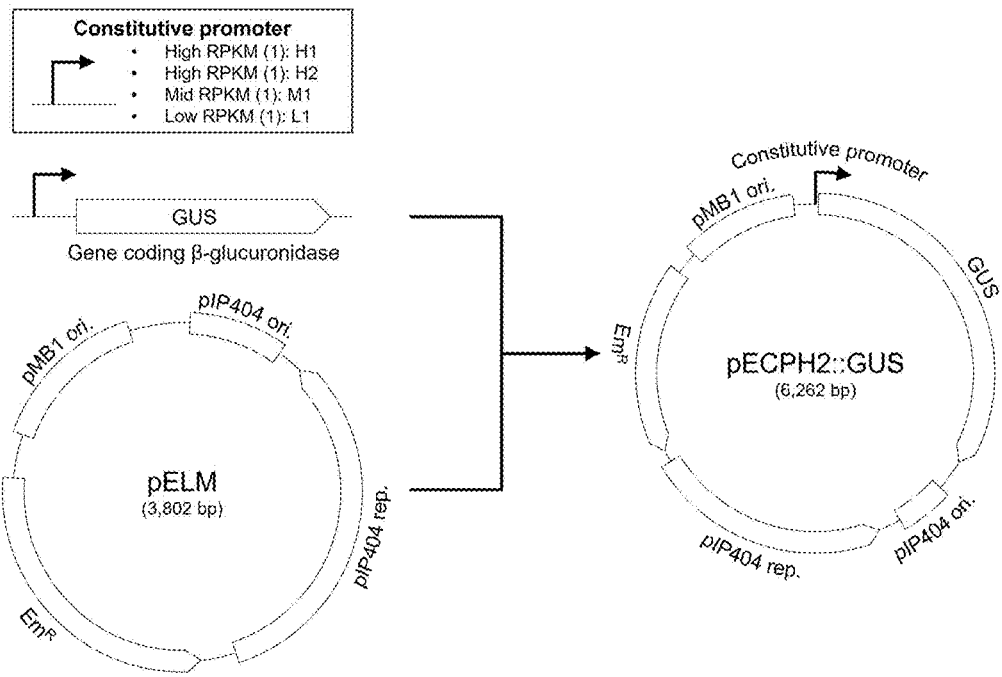
FIG. 3 is a schematic diagram illustrating a cloning process including designating the promoter regions of a upstream the gene having high (H)/middle (M)/low (L) transcript expression values as H1, H2, M1 and L1, respectively, linking the same as promoters to β-glucuronidase (GUS) expression genes to produce insertion genes, and linking the insertion genes to the previously prepared shuttle vector and expression vector customized for the *Eubacterium limosum* KCTC13263BP strain.

Example 3: Determination of Activity of
Autologous Promoter Derived from Eubacterium
limosum KCTC13263BP Strain In order to determine the intensity of the four promoters selected in Example 2, a reporter gene assay was performed. As the reporter gene, a β-glucuronidase (GUS) expression gene of the E. coli BL21 strain was selected. The shuttle vector for the Elm strain prepared in Example 1 was used as a pELM backbone, four promoter candidates (H1, H2, M1, L1) selected in Example 2 were linked to the GUS expression gene to produce insertion gene fragments, and the insertion gene fragments were inserted into the pELM vector to perform cloning (FIG. 3).

The four vectors prepared through cloning were introduced into the Elm strain through the transformation method of Example 1, and the resulting Elm strain transformants were selected in a HBBM-Glc liquid or solid medium containing erythromycin in a final concentration of 120 μg/ml. Whether or not each selected transformant was successfully introduced with the gene was identified based on a wild-type Elm strain as a control group, through colony PCR and plasmid DNA extraction, followed by back-transformation into the E. coli strain, re-extraction of plasmid DNA through the E. coli strain, and treatment of the extracted vector with a specific restriction enzyme.

Figure 4:
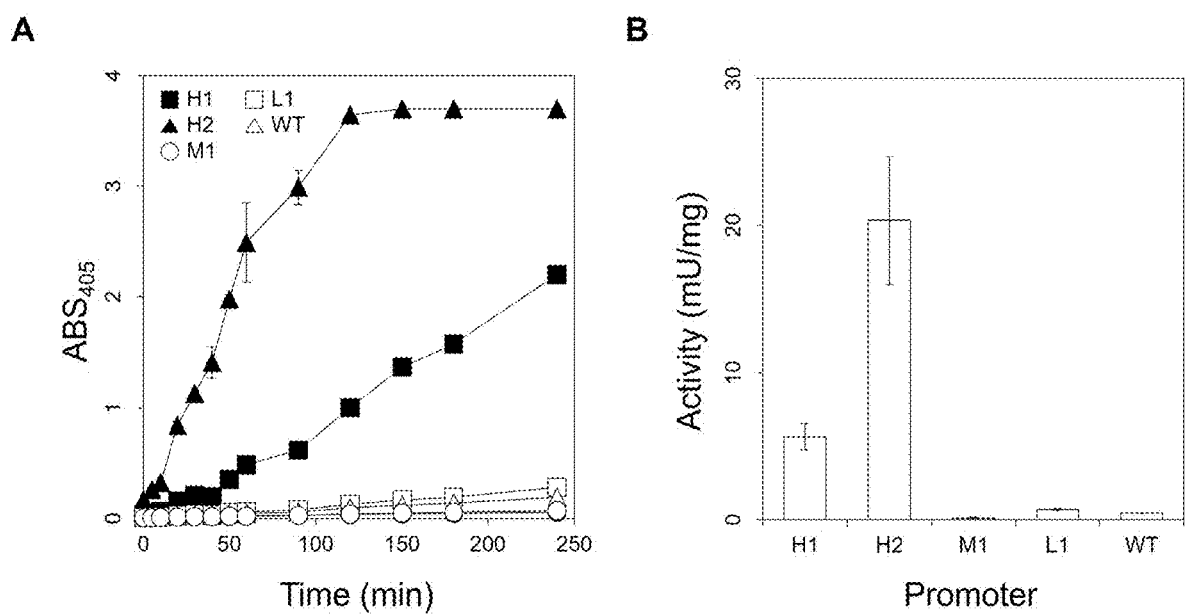
FIG. 4 shows the result of measurement of GUS activity of the four transformants (transformed strains) including respective vectors and the wild-type strain after introducing vectors including four autologous promoters (H1, H2, M1, L1) positioned in front of promoters of GUS-expressing genes into the *Eubacterium limosum* KCTC13263BP strain, wherein A is a graph showing the change in absorbance of each sample at 405 nm and B is a graph showing the GUS activity of the samples derived from the four transformed strains and the wild-type strain.

GUS activity was evaluated through a fluorometric method using 4-NPG (4-nitrophenyl β-D-glucuronide) as a substrate using the identified four Elm strain transformants and the wild-type Elm strain as the control group. The cells in the exponential growth phase of the strain were recovered from the transformant and wild-type Elm strain culture solutions to extract a crude enzyme and a GUS assay was performed using the final 2 mM 4-NPG as a substrate (FIG. 4A). The result showed that the GUS sample expressed by the H2 promoter exhibited the highest activity of 20.35 mU/mg (FIG. 4B), the GUS sample expressed by the H1 promoter that exhibited activity of 5.64 mU/mg, and the GUS samples expressed by the remaining M1 or L1 promoters including the wild-type strain extract exhibited very low activity of 1 mU/mg or less. These results showed that, between promoter candidates H1 and H2 having high expression values based on the transcript analysis result of Example 2, the H2 promoter was finally selected as an autologous promoter for high expression of gene for the Elm strain.

Example 4: Production of Ethanol Through
Introduction of Bifunctional Aldehyde Alcohol
Dehydrogenase (AdhE) into Eubacterium limosum
KCTC13263BP Strain Having No
Ethanol-Producing Ability In this embodiment, in order to convert the Elm strain having no ethanol-producing ability into a transformed strain capable of producing ethanol, the genes (CAETHG_3747, CAETHG_3748) expressing difunctional aldehyde alcohol dehydrogenases (AdhE1, AdhE2) from C.

*autoethanogenum* DSM10061 found to have ethanol-producing ability were selected as target genes to be introduced into the strain.

Each of the selected AdhE1 and AdhE2 genes was linked to the promoter H2, the autologous promoter for high expression of gene for the Elm strain, to synthesize insertion genes for cloning.

Figure 5:
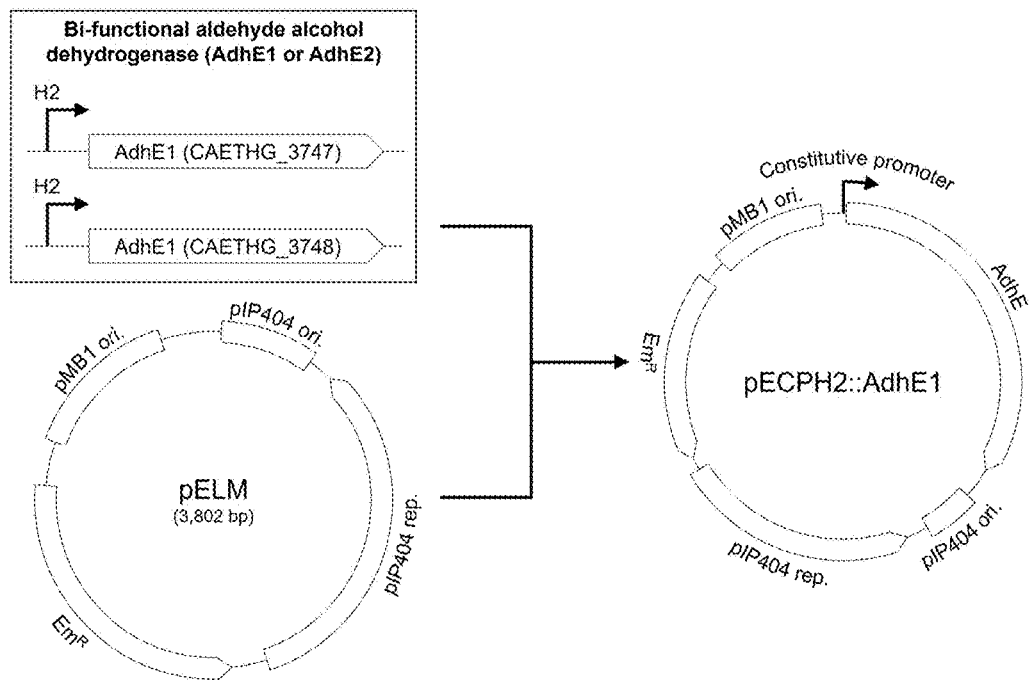
FIG. 5 shows a cloning process of producing a recombinant vector (pECPH2::AdhE1 or pECPH2::AdhE2) by inserting a gene fragment including an H2 promoter positioned in the upstream of genes expressing two bifunctional aldehyde alcohol dehydrogenases (AdhE1, AdhE2) using the shuttle vector pELM for the *Eubacterium limosum* KCTC13263BP strain as a backbone.
Figure 6:
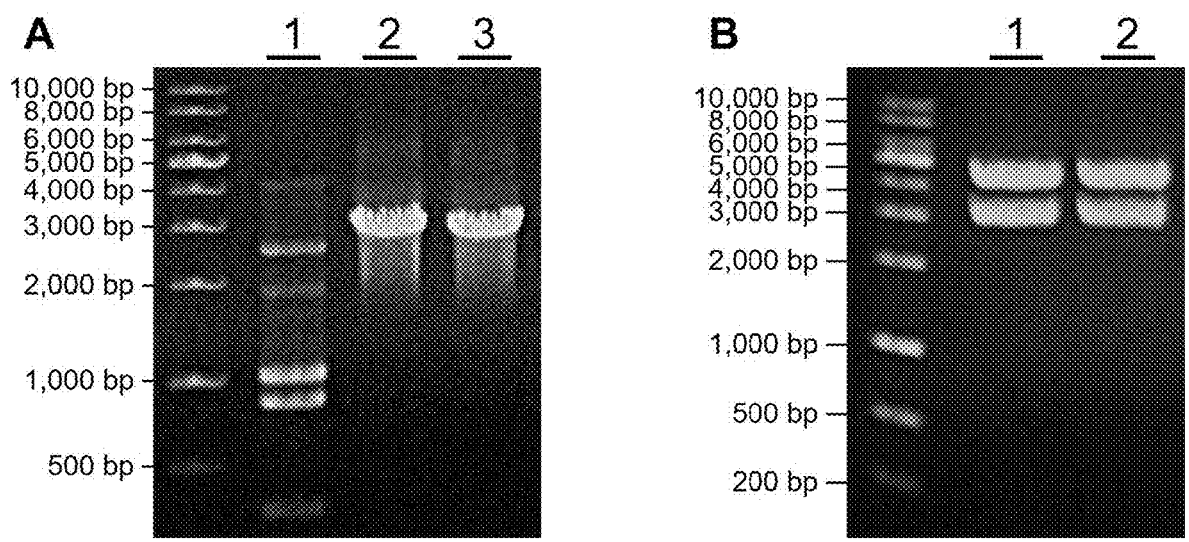
FIG. 6 shows the result of identification of transformed strains introduced with the recombinant vectors (pECPH2::AdhE1 and pECPH2::AdhE2), wherein A shows the result of identification of successful introduction of each recombinant vector through colony PCR on AdhE1 and AdhE2 insertion genes using a corresponding transformed strain cell and B shows the result of measurement of the size of a vector fragment after introducing the vector extracted from each transformant into the *E. coli* strain and treating the re-extracted vector with a restriction enzyme, which indicates that the transformants of the *Eubacterium limosum* KCTC13263BP strain introduced with the respective recombinant vectors were successfully obtained.

Insertion gene fragments including the H2 promoter respectively linked to the AdhE1 gene (SEQ ID NO: 6) and the AdhE2 gene (SEQ ID NO: 7) were inserted into the shuttle vector (pELM) for the Elm strain as the backbone to produce two recombinant vectors, pECPH2::AdhE1 (SEQ ID NO: 8) and pECPH2::AdhE2 (SEQ ID NO: 9) (FIG. 5).

pECPH2::AdhE1 and pECPH2::AdhE2 were introduced into the Elm strain through electroporation, Elm strain transformants containing the respective recombinant vectors were then selected using the same selection method as in Example 3, and the presence of AdhE1 and AdhE2 genes was also identified through a genetic method (FIG. 6). The colony PCR was performed on the inserted genes using the transformants containing AdhE1 and AdhE2, based on other transformants containing the GUS-expressing gene as control groups. As shown in FIG. 6A, the result showed that the PCR product with a desired size can be obtained from only the transformant template containing AdhE1 and AdhE2. In addition, whether or not the strain transformants including AdhE1 and AdhE2 were successfully obtained was identified based on the results of FIG. 6A as well as using methods such as extraction of the plasmid DNA with each AdhE1 or AdhE2-containing transformant culture solution, back-transformation of the extracted vector into the *E. coli* strain, re-extraction of the plasmid DNA from each *E. coli* transformant culture and the treatment of the extracted vector with a specific restriction enzyme (FIG. 6B).

The identified transformed strains were cultured to analyze growth properties and production of metabolites including ethanol in each HBBM-Glc medium and HBBM-CO (CO-based) medium supplemented with erythromycin. At this time, a wild-type Elm strain as a control group was cultured in HBBM-Glc medium and HBBM-CO medium containing no erythromycin.

Figure 7:
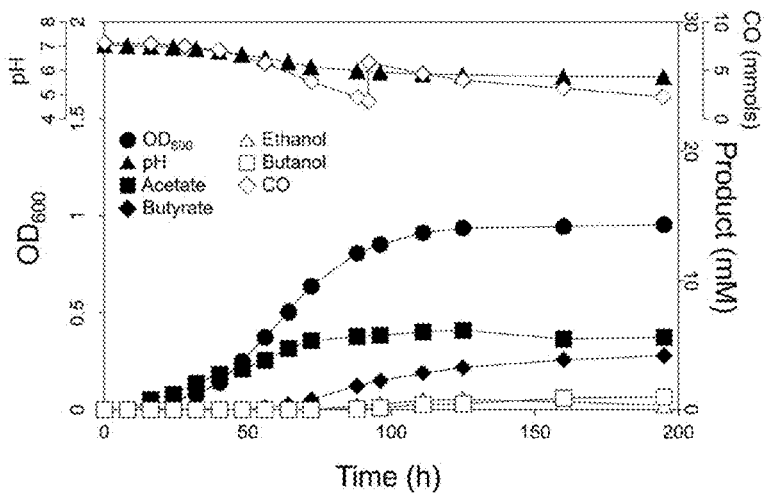
FIG. 7 shows the result of growth and metabolite production analysis under glucose substrate culture conditions of the wild-type *Eubacterium limosum* KCTC13263BP strain and the transformed strains each expressing AdhE1 and AdhE2, wherein A shows the result of growth and metabolite production analysis of the wild-type strain, and B and C show the results of growth and metabolite production analysis of transformed strains each expressing AdhE1 and AdhE2.
Figure 7:
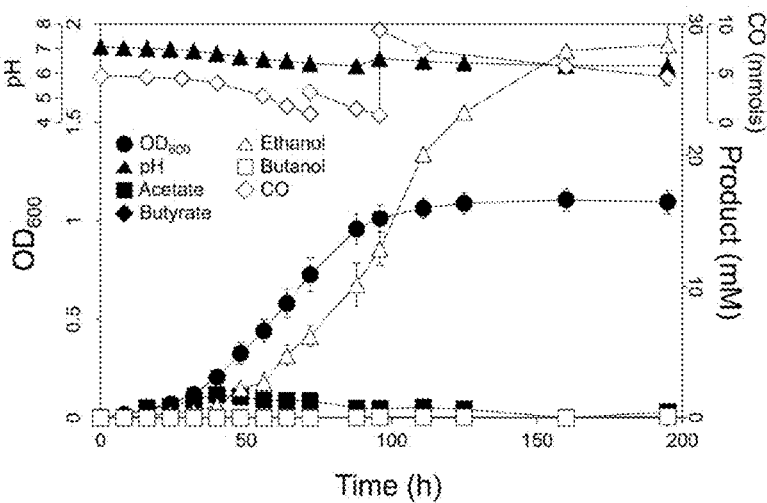
Figure 7:
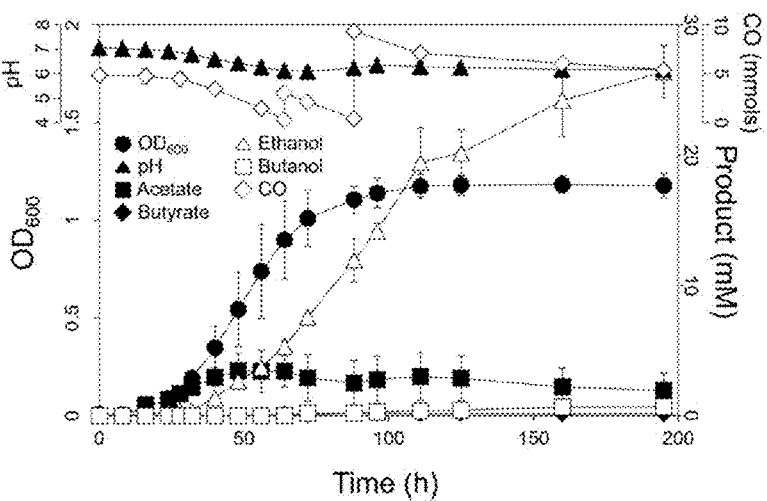

The results of analysis of heterotrophic growth of transformed strains containing AdhE1 or AdhE2 and the wild-type strain under glucose substrate conditions are shown in FIG. 7. As expected, each of the transformed strains containing AdhE1 and AdhE2 (FIGS. 7B and 7C) produced ethanol, unlike the wild-type strain (FIG. 7A), and between the two transformed strains, the transformed strain containing AdhE1 produced a high concentration of ethanol. The transformed strain containing AdhE1 consumed 21.2 mM glucose and produced ethanol up to a concentration of 10.5 mM. There was no significant difference in the strain growth rate or maximal growth ($OD_{max}$) between the wild-type strain and transformed strains, but there was a significant difference therebetween in the production of metabolites such as ethanol and butyrate, except for acetate.

There were no significant differences in acetate production pattern or maximum yield between the wild-type strain and the transformed strains. Almost no butyrate, which is a 4-carbon metabolite of the strain, was produced by an AdhE1-containing transformed strain, but a small amount of butyrate, namely, 1.1 mM, was produced by an AdhE2-containing transformed strain, which was considerably different from 4.5 mM butyrate produced by a wild-type strain. These results suggest that a pathway for producing ethanol and a pathway for producing butyrate from a key intermediate in the catabolic pathway, acetyl-CoA, compete with each other. Then, ethanol in the transformed strain containing AdhE1 or AdhE2 is produced by a route through acetaldehyde directly from acetyl-CoA.

Figure 8:
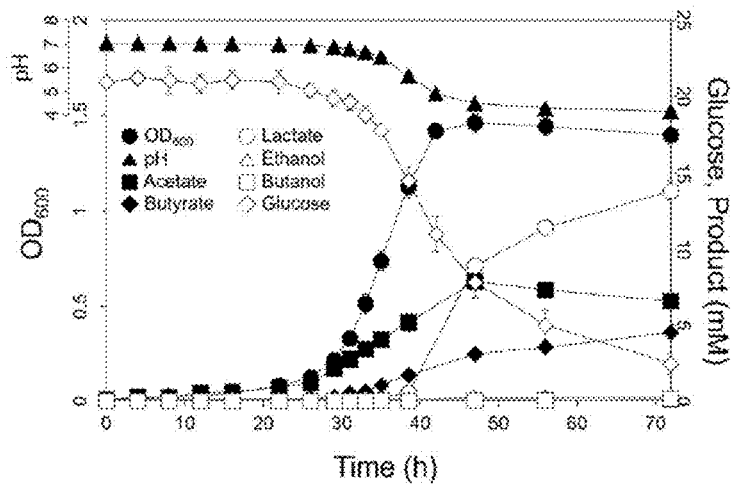
FIG. 8 shows the result of growth and metabolite production analysis under carbon monoxide substrate culture conditions of the wild-type *Eubacterium limosum* KCTC13263BP strain and transformed strains each expressing AdhE1 and AdhE2, wherein A shows the result of growth and metabolite production analysis of the wild-type strain and B and C show the results of growth and metabolite production analysis of the transformed strains each expressing AdhE1 and AdhE2.
Figure 8:
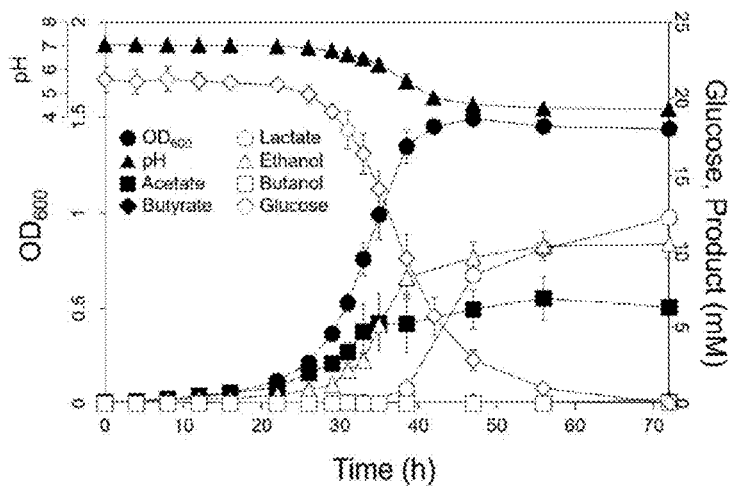
Figure 8:
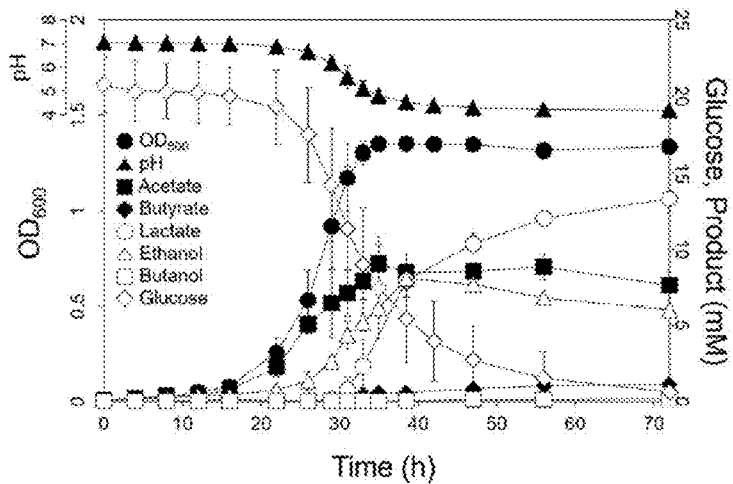

The results of analysis of the autotrophic growth of the transformed strains containing AdhE1 and AdhE2 and the wild-type strain under CO substrate conditions are shown in FIG. 8. Like the glucose substrate condition, the production of ethanol was not detected in the wild-type strain (FIG. 8A), but ethanol was produced only in the transformed strains (FIG. 8B, FIG. 8C). Both transformed strains containing AdhE1 and AdhE2, which are transformed strains, consumed a total of 11.5 mmol of CO and thus produced ethanol at a concentration of up to 28 mM. Among them, the transformed strain containing AdhE1 reached the maximum ethanol production at a higher rate. Interestingly, unlike under the glucose substrate conditions, under the CO substrate conditions, all of the transformed strains clearly produced acetate, the main metabolite of the strain, and then consumed the same. The transformed strain containing AdhE1 produced acetate at a concentration of up to 1.8 mM only in the initial growth stage, and thus consumed the acetate again and production thereof reached the background level and thus was not detected after the stationary phase. These results indicate that acetate was produced after the initial growth stage, but production of acetate was not detected because the production rate of ethanol through acetate reuse is equal to or higher than the production rate of acetate after the initial growth stage.

Like the AdhE1-containing transformed strain described above, the AdhE2-containing transformed strain also produced acetate and consumed the same again. However, the AdhE2-containing transformed strain consumed acetate at a lower rate than the AdhE1-containing transformed strain and could not completely consumed acetate even after the stationary phase. In addition, neither transformed strain produced butyrate during growth. There was no significant difference in growth rate or maximal growth ($OD_{max}$) between the wild-type and transformed strains, like under the glucose substrate conditions.

In previous studies conducted on Elm strains, lactate production of Elm strains has been neither disclosed nor analyzed, but the present invention identified that the Elm strain produced both L-lactate and D-lactate, and the L-form and D-form were produced at a ratio of about 1:1.5 under 20 mM glucose substrate conditions such that total lactate reached about 13 mM. Moreover, it was identified that lactate was not produced under autotrophic CO substrate conditions, but was produced only under heterotrophic glucose substrate conditions. The genetic information in the strain showed that lactate is produced from pyruvate in the presence of a catalyst of lactate dehydrogenase (LDH; ELI_3346, ELI_4443). At this time, NADH acts as an electron donor. That is, the production of lactate from pyruvate requires only the same reducing power as NADH, and is a reaction that does not involve any energy conservation. Lactate is produced for effective reducing power consumption due to the $NAD^+$/NADH balance thereof, because ATP and reduced NADH are produced sufficiently under heterotrophic glucose substrate conditions through glycolysis. Meanwhile, autotrophic CO gas metabolic pathways are reactions that consume NADH and ATP and thus produce no lactate, unlike heterotrophic substrate conditions.

Figure 9:
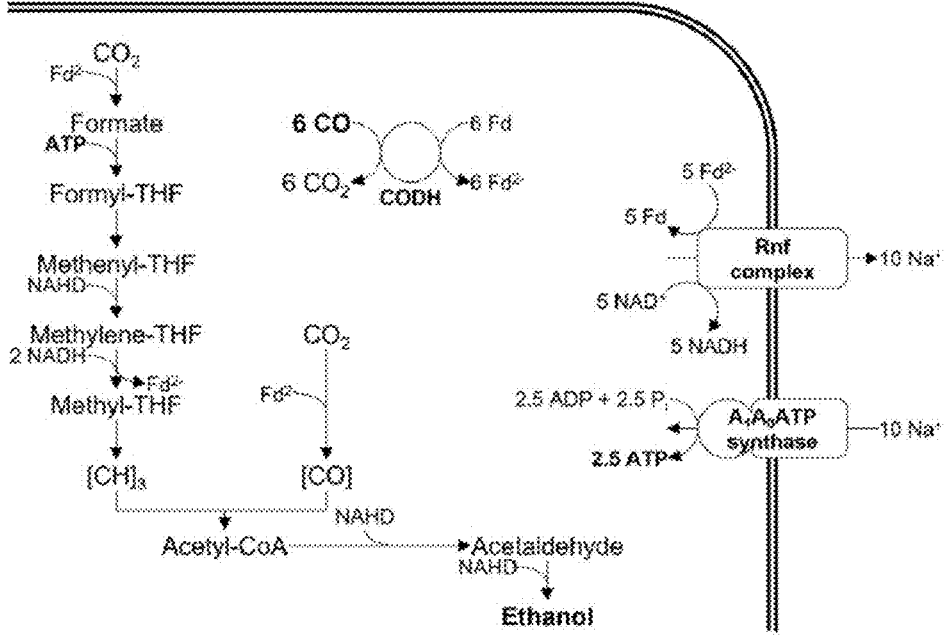
FIG. 9 shows two possible ethanol production pathways in the transformed strain expressing AdhE1 or AdhE2 under carbon monoxide substrate culture conditions and ATP produced relative to carbon monoxide substrate consumption in each pathway, wherein A is a pathway for producing ethanol directly through acetaldehyde from acetyl-CoA in the presence of an AdhE1 enzyme or AdhE2 enzyme as a catalyst, and B is an acetate reuse ethanol production pathway including producing acetaldehyde using aldehyde ferredoxin oxidoreductase (AOR; ELI_0332, ELI_1752, ELI_3389) originally possessed by the strain in a manner that reuses acetate and converting the acetaldehyde to ethanol using the enzyme AdhE1 or AdhE2.
Figure 9:
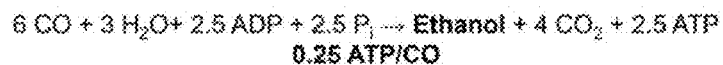
Figure 9:
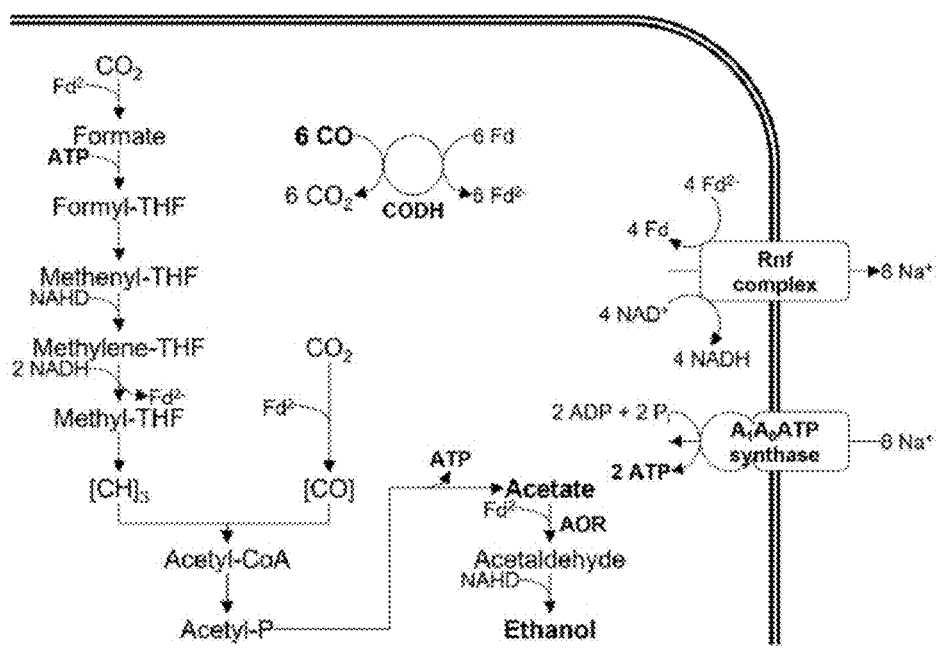
Figure 9:

Example 5: Ethanol Production Pathway and Bioenergetics Model in *Eubacterium limosum* KCTC13263BP Transformed Strain Producing Ethanol Using CO Substrate CO substrate-based ethanol production using the Elm transformed strain prepared in Example 4 is possible through two pathways, that is, a pathway for producing ethanol directly through acetaldehyde from acetyl-CoA (FIG. 9A) and a pathway including first producing acetate, then synthesizing acetaldehyde by re-using the produced acetate through AOR and producing ethanol (FIG. 9B). The two pathways are the same as each other in the synthesis of acetyl-CoA from CO and in the production of ethanol from acetaldehyde, but differ from each other in the synthesis of acetaldehyde from acetyl-CoA.

The pathway for synthesizing acetaldehyde from acetyl-CoA as shown in FIG. 9A requires the same molecule of NADH per one molecule of acetyl-CoA, and the pathway including first producing acetate from acetyl-CoA and then synthesizing acetaldehyde by re-using the produced acetate, as shown in FIG. 9B, requires the same number of molecule of reduced ferredoxin ($Fd^{2-}$) per one molecule of acetyl-CoA and, at the same time causes the production of the same molecule of ATP. When $Fd^{2-}$ is used instead of NADH as a reducing equivalent in the catabolic metabolism, less oxidation of $Fd^{2-}$ occurs in the Rnf complex as chemiosmotic energy conservation (CEC) based on redox balancing. Thus, the resulting $NAD^+$ reduction reaction and ion ($Na^+$ or $H^+$)-motive force generation also less occur, eventually resulting in production of less ATP by the CEC mechanism in the case where $Fd^{2-}$ is used (FIG. 9B), compared to the case where NADH is used as a reducing equivalent (FIG. 9A). However, the case of producing ethanol by reusing acetate, as in the route shown in FIG. 9B, is capable of obtaining ATP by substrate-level phosphorylation through acetate production, thus providing a higher total ATP production, even though the amount of ATP produced by the CEC mechanism is smaller than that of the route shown in FIG. 9A. In conclusion, the production of ethanol through acetate reuse is capable of obtaining ATP through substrate-level phosphorylation during the synthesis of acetate from acetyl-CoA and is thus more energy-efficient.

The most significant result of the present invention is based on the fact that the Elm transformed strain containing AdhE1-expressing genes is capable of converting acetaldehyde to ethanol by directly reusing acetate, which is the main metabolite of the wild-type strain, under autotrophic CO substrate conditions, and is capable of producing only ethanol without producing another metabolite, namely, butyrate.

In addition, it was proved that the transformed strain containing AdhE1 produced ethanol at a significant concentration of about 28 mM without the manipulation of genomic DNA under autotrophic substrate conditions, rather than under heterotrophic substrate conditions. The transformed strain containing AdhE1 obtained by the present invention is expected to act as a very promising biocatalyst in terms of industrial applicability when applied to a synthetic gas process in the future, since a product separation step in the downstream of the synthetic gas process can be omitted or simplified.

INDUSTRIAL APPLICABILITY

According to the present invention, value-added ethanol can be produced from carbon monoxide contained in waste gas using *Eubacterium limosum* KCTC13263BP, which is a conventional acetogen having no ethanol-producing ability.

Although specific configurations of the present invention have been described in detail, those skilled in the art will appreciate that this description is provided to set forth preferred embodiments for illustrative purposes and should not be construed as limiting the scope of the present invention. Therefore, the substantial scope of the present invention is defined by the accompanying claims and equivalents thereto.

[Sequence Listing Free Text]

An electronic file is attached.

The invention claimed is:

1. A transformed *Eubacterium limosum* strain having ethanol-producing ability, in which AdhE1 or AdhE2 being a gene encoding a bifunctional aldehyde alcohol dehydrogenase is introduced into *Eubacterium limosum* having no ethanol-producing ability.

2. The transformed *Eubacterium limosum* strain according to claim 1, wherein the AdhE1 or AdhE2 is from *Clostridium autoethanogenum, C. ljungdahlii*, or *C. carboxidivorans*.

3. The transformed *Eubacterium limosum* strain according to claim 1, wherein a transcription of the gene encoding the bifunctional aldehyde alcohol dehydrogenase is regulated by a promoter having the nucleotide sequence of SEQ ID NO: 2.

4. The transformed *Eubacterium limosum* strain according to claim 1, wherein the *Eubacterium limosum* is a *Eubacterium limosum* KCTC13263BP strain.

5. The transformed *Eubacterium limosum* strain according to claim 1, wherein the gene is introduced by (a) using a shuttle vector pELM having the nucleotide sequence of SEQ ID NO: 1 as a backbone; (b) producing an insertion gene fragment by linking a promotor with the gene; and (c) inserting the insertion gene fragment into a pELM vector for cloning.

6. A method of preparing ethanol comprising:
(a) culturing the transformed *Eubacterium limosum* strain according to claim 1 in the presence of a carbon monoxide-containing gas to produce ethanol; and
(b) recovering the produced ethanol.

7. A vector for expressing a *Eubacterium limosum* strain comprising the constitutive strong promoter having the nucleotide sequence of SEQ ID NO: 2 or SEQ ID NO: 3, and a shuttle vector backbone represented by a having the nucleotide sequence of SEQ ID NO: 1.

* * * * *

UNITED STATES PATENT AND TRADEMARK OFFICE
CERTIFICATE OF CORRECTION

PATENT NO. : 11,976,314 B2
APPLICATION NO. : 16/643126
DATED : May 7, 2024
INVENTOR(S) : In Seop Chang et al.

It is certified that error appears in the above-identified patent and that said Letters Patent is hereby corrected as shown below:

In the Claims

Column 34, Line 52, "a shuttle vector backbone represented by a having the" should be
-- a shuttle vector backbone having the --.

Signed and Sealed this
Twenty-second Day of October, 2024

Katherine Kelly Vidal
*Director of the United States Patent and Trademark Office*

SEQUENCE LISTING

```
<160> NUMBER OF SEQ ID NOS: 9

<210> SEQ ID NO 1
<211> LENGTH: 3802
<212> TYPE: DNA
<213> ORGANISM: Artificial Sequence
<220> FEATURE:
<223> OTHER INFORMATION: shuttle vector pELM

<400> SEQUENCE: 1
gaatcaacaa ctctcctggc tagctagcta gcagaagttg cagaattaag aagacaacaa      60
ggacaagcaa aacattaagc attttgcctt cctgtttttg ctcacccaga aacgctggtg     120
aaagtaaaag atgctgaaga tcagttgggt gcacgagtgg gttacatcga actggatctc     180
aacagcggta agatccttga gagttttcgc cccgaagaac gttttccaat gatgagcact     240
tttatcaaaa aaatttccaa taatcccact ctaagccaca aacacgccct ataaaatccc     300
gctttaatcc cactttgaga cacatgtaat attactttac gccctagtat agtgataatt     360
ttttacattc aatgccacgc aaaaaaataa aggggcacta taataaaagt tccttcggaa     420
ctaactaaag taaaaaatta tctttacaac ctccccaaaa aaagaacag gtacaaagta     480 ccctataata caagcgtaaa aaaaatgagg gtaaaaataa aaaaataaaa aaataaaaaa     540
ataaaaaaat ataaaaataa aaaaataaaa aaatataaaa atattttta tttaaagttt     600 gaaaaaaatt ttttatatt atataatctt tgaagaaaag aatataaaaa atgagccttt     660
```

```
ataaaagccc atttttttc atatacgtaa tatgacgttc taatgttttt attggtactt      720
ctaacattag agtaatttct ttatttttaa agccttttc tttaagggct tttattttt       780 ttcttaatac atttaattcc tcttttttg ttgcttttcc tttagctttt aattgctctt      840
gataattttt tttacctcta atattttctc ttctcttata ttccttttta gaaattatta    900
ttgtcatata ttttgttct tcttctgtaa tttctaataa ctctataaga gtttcattct     960
tatacttata ttgcttattt ttatctaaat aacatcttc agcacttcta gttgctctta    1020
taacttctct ttcacttaaa tgttgtctaa acatactatt aagttctaaa acatcattta    1080
atgccttctc aatgtcttct gtaaagctac aaagataata tctatataaa aataatataa    1140
gctctctgtg tccttttaaa tcatattctc ttagttcaca aagttttatt atgtcttgta    1200
ttcttccata atataaactt ctttctctat aaatataatt tattttgctt ggtctaccct    1260 ttttccttc atatggtttt aattcaggta aaaatccatt ttgtatttct cttaagtcat     1320
aaatatattc gtactcatct aatatattga ctactgtttt tgatttagag tttatacttc    1380
ctggaactct taatattctc gttgcatcta aggcttgtct atctgctcca aagtatttta    1440
attgattata taaatattct tgaaccgctt tccataatgg taatgcttta ctaggtactg    1500
catttattat ccatattaaa tacattcctc ttccactatc tattacatag tttggtatag    1560
gaatactttg attaaaataa ttcttttcta agtccattaa tacctggtct ttagttttgc    1620
cagttttata ataatccaag tctataaaca gtgtatttaa ctcttttata ttttctaatc    1680
gcctacacgg cttataaaag gtatttagag ttatatagat attttcatca ctcatatcta    1740
aatcttttaa ttcagcgtat ttatagtgcc attggctata tccttttta tctataacgc     1800 tcctggttat ccacccttta cttctactat gaatattatc tatatagttc tttttattca    1860
gctttaatgc gtttctcact tattcacctc ccctccctt agtaacgtgt aactttccaa     1920
atttacaaaa gcgactcata gaattatttc ctcccgttaa ataatagata actattaaaa    1980
atagacaata cttgctcata agtaacggta cttaaattgt ttactttggc gtgtttcatt    2040
gcttgatgaa actgattttt agtaaacagt tgacgatatt ctcgattgac ccattttgaa    2100
acaaagtacg tatatagctt ccaatatta tctggaacat ctgtggtatg gcgggtaagt     2160
tttattaaga cactgtttac tttggttta ggatgaaagc attccgctgg cagcttaagc     2220
aattgctgaa tcgagacttg agtgtgcaag agcaaccca tgttcggtg aatatccaag      2280 gtacgcttgt agaatccttc ttcaacaatc agatagatgt cagacgcatg gctttcaaaa    2340 accactttt taataattg tgtgcttaaa tggtaaggaa tactcccaac aattttatac      2400
ctctgtttgt tagggaattg aaactgtaga atatcttggt gaattaaagt gacacgagta    2460
ttcagtttta attttctga cgataagttg aatagatgac tgtctaattc aatagacgtt     2520
acctgtttac ttattttagc cagtttcgtc gttaaatgcc ctttacctgt tccaatttcg    2580
taaacggtat cggtttcttt taaattcaat tgttttatta tttggttgag tacttttca     2640 ctcgttaaaa agttttgaga atattttata tttttgttca tgtaatcact ccttcttaat    2700
tacaaatttt tagcatctaa tttaacttca attcctatta tacaaaattt taagatactg    2760
cactatcaac acactcttaa gttgcttct aagtcttatt tccataactt cttttacgtt     2820
tccgggtaca attcgtaatc atgtcatagc tgtttcctgt gtgaaattgt tatccgctca    2880
caattccaca caacatacga gccggaagca taaagtgtaa agcctggggt gcctaatgag    2940
tgagctaact cacattaatt gcgttgcgct cactgcccgc tttccagtcg ggaaacctgt    3000
```

| | |
|---|---|
| cgtgccagaa aaggatctag gtgaagatcc tttttgataa tctcatgacc aaaatccctt | 3060 |
| aacgtgagtt ttcgttccac tgagcgtcag accccgtaga aaagatcaaa ggatcttctt | 3120 |
| gagatccttt ttttctgcgc gtaatctgct gcttgcaaac aaaaaaacca ccgctaccag | 3180 |
| cggtggtttg tttgccggat caagagctac caactctttt tccgaaggta actggcttca | 3240 |
| gcagagcgca gataccaaat actgttcttc tagtgtagcc gtagttaggc caccacttca | 3300 |
| agaactctgt agcaccgcct acatacctcg ctctgctaat cctgttacca gtggctgctg | 3360 |
| ccagtggcga taagtcgtgt cttaccgggt tggactcaag acgatagtta ccggataagg | 3420 |
| cgcagcggtc gggctgaacg gggggttcgt gcacacagcc cagcttggag cgaacgacct | 3480 |
| acaccgaact gagataccta cagcgtgagc tatgagaaag cgccacgctt cccgaaggga | 3540 |
| gaaaggcgga caggtatccg gtaagcggca gggtcggaac aggagagcgc acagggagc | 3600 |
| ttccaggggg aaacgcctgg tatctttata gtcctgtcgg gtttcgccac ctctgacttg | 3660 |
| agcgtcgatt tttgtgatgc tcgtcagggg gcggagcct atggaaaaac gccagcaacg | 3720 |
| cggcctttt acggttcctg gccttttgct ggccttttgc tcacatgttc tttcctgcgt | 3780 |
| tatcccctga ttctgactag tc | 3802 |

```
<210> SEQ ID NO 2
<211> LENGTH: 110
<212> TYPE: DNA
<213> ORGANISM: Artificial Sequence
<220> FEATURE:
<223> OTHER INFORMATION: promoter H2

<400> SEQUENCE: 2
```

| | |
|---|---|
| ttttccgttt aaagtttaaa aattgtggta taattaatta tatcattaag cggataagtg | 60 |
| ggttacacgg actgctcaaa attatatttg gactatagga ggtctttatt | 110 |

```
<210> SEQ ID NO 3
<211> LENGTH: 110
<212> TYPE: DNA
<213> ORGANISM: Artificial Sequence
<220> FEATURE:
<223> OTHER INFORMATION: promoter H1

<400> SEQUENCE: 3
```

| | |
|---|---|
| tttttttatg taaaaagtt agttaaaaat aacaaaatta atgataatca agaaaaagt | 60 |
| gggtataatt aaagatagcg aaataggaaa ccaatacagg aggaaaaaga | 110 |

```
<210> SEQ ID NO 4
<211> LENGTH: 96
<212> TYPE: DNA
<213> ORGANISM: Artificial Sequence
<220> FEATURE:
<223> OTHER INFORMATION: promoter M1

<400> SEQUENCE: 4
```

| | |
|---|---|
| gcttttgcct atcttttaa ttatataata ctatttgcca aactcattcc actaaagtac | 60 |
| aatagaatca tcaaatctca cacaaaggat ttttat | 96 |

```
<210> SEQ ID NO 5
<211> LENGTH: 100
<212> TYPE: DNA
<213> ORGANISM: Artificial Sequence
<220> FEATURE:
<223> OTHER INFORMATION: promoter L1

<400> SEQUENCE: 5
```

-continued

| | |
|---|---|
| gtatttggat ggggatcttc cttgacgctt taagggga ct ccgatatgat gaaatcaacc | 60 |
| aaacagacaa atctcaagat taagaaggag acacatattc | 100 |

<210> SEQ ID NO 6
<211> LENGTH: 2613
<212> TYPE: DNA
<213> ORGANISM: Artificial Sequence
<220> FEATURE:
<223> OTHER INFORMATION: AdhE1

<400> SEQUENCE: 6

| | |
|---|---|
| atgaaagtta caaacgtaga agaactaatg aaaagactag aagaaataaa ggatgctcaa | 60 |
| aagaaatttg ctacatatac tcaagaacaa gtggatgaaa ttttagaca agcagctatg | 120 |
| gcagctaata gtgctagaat agaactagct aaaatggcag tagaagaaag cggaatggga | 180 |
| attgtagaag acaaggttat taaaaatcac tttgcttcag aatatatata taacaaatat | 240 |
| aaggatgaaa aaacctgtgg agttttagag agagatgcag gctttggtat agttagaatt | 300 |
| gcggaacctg taggagttat tgcagcagta gttccaacaa ctaatccaac atctacagca | 360 |
| atatttaaat cactaatagc tttaaaaact agaaatggta taattttttc accccatcca | 420 |
| agggcaaaga atcaactat gcagcagct aaaatagtac ttgacgctgc agttaaagct | 480 |
| ggtgctcctg aaggaattat aggatggata gatgaacctt ccattgaact ttcacaggtg | 540 |
| gtaatgggag aagcaaattt aattcttgca actggtggtc cgggtatggt taaggctgcc | 600 |
| tattcttcag gcaaacctgc tgtgggagtt ggtccaggta acacacctgc tgtaattgat | 660 |
| gaaagtgccg acattaaat ggcagtaaat tcaatattac tatcaaaaac ttttgataat | 720 |
| ggtatgattt gtgcctcaga gcagtcagta atagttttag actcaatata tgaggaagtt | 780 |
| aaaaagaat ttgcttatag gggtgcttat atattaagta aggatgaaac agataaggtt | 840 |
| ggaaaaataa ttttaaaaaa tggagcctta aatgcaggta ttgtaggaca acctgctttt | 900 |
| aaaatagcac agctggcagg agtggatgta ccagaaaaag ctaaagtact tataggagag | 960 |
| gtagaatcgg tagaacttga agaaccattt tctcatgaaa agttatctcc agttttagct | 1020 |
| atgtacaggg caagaaattt tgaggatgcc attgcaaaa ctgataaact ggttagggca | 1080 |
| ggtggatttg acatacatc ttcattgtat ataaatccaa tgacagaaaa agcaaaagta | 1140 |
| gaaaattta gtactatgat gaaaacatca agaactaaa ttaacacacc ttcatcccaa | 1200 |
| ggtggtatag gtgatatata aactttaaa ctagctcctt ctttgacatt aggctgcggt | 1260 |
| tcctgggggg gaaattctgt atccgaaaat gttgggccta acatttatt aaacataaaa | 1320 |
| agtgttgctg agaggagaga aaatatgctt tggtttagag tacctgaaaa ggtttatttc | 1380 |
| aaatatggta gtcttggagt tgcattaaaa gagttaaaag ttatgaataa gagaaagta | 1440 |
| tttatagtaa cagataaagt tctttatcaa ttaggttatg tggacaaagt tacaaaagtt | 1500 |
| cttgaggaac taaaaatttc ctataaggta tttacagatg tagaaccaga tccaacccctt | 1560 |
| gctacagcta aaaaaggtgc agcagaactg ctttcctatg aaccggatac aattatatca | 1620 |
| gttggtggtg gttcagcaat ggatgcagct aagatcatgt gggtaatgta tgagcatcca | 1680 |
| gaagtaaat ttgaagattt agctatgaga tttatggata taagaaagag agtatatgtt | 1740 |
| ttccctaaga tgggagaaaa ggcaatgatg atttcagtag caacatccgc aggaacaggg | 1800 |
| tcggaagtta ctccattgc agtaatcact gatgaaaaaa caggagctaa atatccatta | 1860 |
| gctgattatg aactaactcc agacatggct atagttgatg cagaacttat gatgggaatg | 1920 |

| | |
|---|---|
| ccaagaggac ttacagcagc ttcgggtata gatgcattaa cccatgcact ggaggcgtat | 1980 |
| gtgtcaataa tggctacaga atttaccaat ggattagccc ttgaagcagt aaagttgata | 2040 |
| tttgaatatt taccaaaagc ttatacagaa ggtacaacta atgtaaaggc aagagaaaag | 2100 |
| atggctcatg cttcatgtat tgcaggtatg gcctttgcaa atgcattttt aggggtatgc | 2160 |
| cactctatgg cacataaatt gggagcacag catcacatac cacatggaat tgccaatgca | 2220 |
| cttatgatag atgaagttat aaaattcaat gctgtagatg atccaataaa acaagctgca | 2280 |
| tttccccaat acgagtatcc aaatgctagg tatagatatg ctcagatagc tgattgtctg | 2340 |
| aacttgggag gaaatacaga agaggaaaag gtacaactat taataaatgc tatagatgat | 2400 |
| ttaaaagcta agttaaatat tccagaaact ataaaagaag caggagtttc agaagataaa | 2460 |
| ttctatgcta ctttagataa aatgtcagaa ttagcttttg atgatcagtg tacaggagct | 2520 |
| aatccaagat atccactgat aagtgaaata aaacaaatgt atataaatgt ttttgataaa | 2580 |
| accgaaccaa ttgtagaaga tgaagaaaag taa | 2613 |

<210> SEQ ID NO 7
<211> LENGTH: 2634
<212> TYPE: DNA
<213> ORGANISM: Artificial Sequence
<220> FEATURE:
<223> OTHER INFORMATION: AdhE2

<400> SEQUENCE: 7

| | |
|---|---|
| atgaaggtaa ctaaggtaac taacgttgaa gaattaatga aaagttaga tgaagtaacg | 60 |
| gctgctcaaa agaatttttc tagctatact caagaacaag tggatgaaat ttcaggcag | 120 |
| gcagctatgg cagccaatag tgctagaata gacttagcta aatggcagt ggaagaaagc | 180 |
| ggaatgggaa ttgtagaaga caaggtcatt aaaaatcatt tgttgcaga atatatatat | 240 |
| aacaaatata agggtgaaaa gacctgcgga gttctggaac aagatgaagg ctttggtatg | 300 |
| gttagaattg cagaacctgt aggagttatt gcagcagtag ttccaacaac taatccaaca | 360 |
| tctacagcaa tatttaaatc actaatagct ttaaaaacta gaaatggtat agttttttca | 420 |
| ccacatccaa gggcaaaaaa atcaactatt gcagcagcta gatagtact tgatgcagca | 480 |
| gttaaagctg gtgcccctga aggaattata ggctggatag atgaaccttc tattgaactt | 540 |
| tcacaggtgg taatgaaaga agcagatcta attcttgcaa ctggtggacc aggtatggtt | 600 |
| aaggctgcct attcttcagg aaagcctgct ataggagttg gtccaggtaa tacacctgct | 660 |
| gtaattgatg aaagtgccga cattaaaatg gcagtaaatt caatactact ttcaaaaact | 720 |
| tttgataatg gtatgatttg tgcttcagag cagtcagtaa tagttgcaag ctcaatatac | 780 |
| gatgaagtca agaagagtt tgcagataga ggagcatata tattaagtaa ggatgaaaca | 840 |
| gataaggttg gaaaaacaat catgattaat ggagctttaa atgctggaat tgtagggcaa | 900 |
| agtgccttta aaatagctca gatggcggga gtcagtgtac cggaagatgc taaaatactt | 960 |
| ataggagaag ttaaatcggt agaacctgaa gaagagccct tgctcatga aaagctgtct | 1020 |
| ccagttctag ccatgtacaa agcaaagat tttgatgaag cacttctaaa ggctggaaga | 1080 |
| ttagttgaac gaggtggaat agggcataca tctgtattgt atgtaaattc gatgacggaa | 1140 |
| aaagtaaaag tagaaaagtt cagagaaact atgaagaccg tagaacatt gataaatatg | 1200 |
| ccttcagcgc aaggcgctat aggagatata taaactttta actagctccc ttctttgaca | 1260 |
| ttaggctgtg gttcctgggg aggaaactct gtatcagaaa atgttggacc taaacatttg | 1320 |
| ttaaacataa agagtgttgc tgagaggaga gaaaatatgc tttggttag agtacctgaa | 1380 |

| | |
|---|---|
| aaggtttatt tcaaatatgg cagccttgga gttgcactaa agaactgag aattatggag | 1440 |
| aagaaaaagg cgtttatagt aacgataaa gttctttatc aattaggtta tgtagataaa | 1500 |
| attacaaaga acctcgatga attaagagtt tcatataaaa tatttacaga tgtagaacca | 1560 |
| gatccaaccc ttgctacagc taaaaaaggt gcagcagaac tgctttccta tgaaccagat | 1620 |
| acaattatag cagttggtgg tggttcggca atggatgctg ccaagatcat gtgggtaatg | 1680 |
| tatgagcatc cagaagtaag atttgaagat ttggccatga gatttatgga tataagaaag | 1740 |
| agagtatatg tttttcctaa gatgggagaa aaggcaatga tgatttcagt agcaacatcc | 1800 |
| gcaggaacag ggtcagaagt tactccattt gcagtaatta cggacgaaag aacaggagct | 1860 |
| aaatatcctc tggctgatta tgaattaact ccaaacatgg ctatagttga tgcagaactt | 1920 |
| atgatgggaa tgccaaaggg gctaacagca gcttcaggta tagatgcgtt gactcatgca | 1980 |
| ctggaggcct atgtgtcaat aatggcttca gaatatacca acggattggc tcttgaagca | 2040 |
| acaagattag tattcaaata tttgccaata gcttatacag aaggtacaat taatgtaaag | 2100 |
| gcaagagaaa aaatggctca tgcttcatgt attgcaggta tggcctttgc caatgcattt | 2160 |
| ttaggggtat gccactctat ggcacataaa ttgggagcac agcaccacat accacatgga | 2220 |
| attgccaatg cacttatgat agatgaagtt ataaaattca atgctgtaga ggctccaagg | 2280 |
| aaacaagcgg catttccaca atataaatat ccaaatgtta aaagaagata tgctagaata | 2340 |
| gctgattacc taaatttagg tggaagtaca gatgatgaaa aagtacaatt gctaataaat | 2400 |
| gctatagatg acttaaaaac taagttaaat attccaaaga ctattaaaga agcaggagtt | 2460 |
| tcagaagata aattctatgc tactttagat acaatgtcag aactggcttt tgatgatcaa | 2520 |
| tgtacaggag ctaatccacg atatccacta ataggagaaa taaaacaaat gtatataaat | 2580 |
| gcatttgata caccaaaggc aactgtggag aagaaaacaa gaaagaaaaa gtaa | 2634 |

<210> SEQ ID NO 8
<211> LENGTH: 6741
<212> TYPE: DNA
<213> ORGANISM: Artificial Sequence
<220> FEATURE:
<223> OTHER INFORMATION: pECPH2::AdhE1

<400> SEQUENCE: 8

| | |
|---|---|
| gactagtccc gaaaagtgcc acctgttatt cctttcttga tattattcta atttcaaaca | 60 |
| aaattttata ggcattttcc gtttaaagtt taaaattgt ggtataatta attatatcat | 120 |
| taagcggata agtgggttac acggactgct caaaattata tttggactat aggaggtctt | 180 |
| tattatgaaa gttacaaacg tagaagaact aatgaaaaga ctagaagaaa taaaggatgc | 240 |
| tcaaagaaa tttgctacat atactcaaga acaagtggat gaaatttta gacaagcagc | 300 |
| tatggcagct aatagtgcta gaatagaact agctaaaatg gcagtagaag aaagcggaat | 360 |
| gggaattgta agacaagg ttattaaaaa tcactttgct tcagaatata tatataacaa | 420 |
| atataaggat gaaaaaacct gtggagtttt agagagagat gcaggctttg gtatagttag | 480 |
| aattgcggaa cctgtaggag ttattgcagc agtagttcca acaactaatc caacatctac | 540 |
| agcaatattt aaatcactaa tagctttaaa aactagaaat ggtataattt tttcaccca | 600 |
| tccaagggca aagaaatcaa ctattgcagc agctaaaata gtacttgacg ctgcagttaa | 660 |
| agctggtgct cctgaaggaa ttataggatg gatagatgaa ccttccattg aactttcaca | 720 |
| ggtggtaatg ggagaagcaa atttaattct tgcaactggt ggtccgggta tggttaaggc | 780 |

```
tgcctattct tcaggcaaac ctgctgtggg agttggtcca ggtaacacac ctgctgtaat    840
tgatgaaagt gccgacatta aaatggcagt aaattcaata ttactatcaa aaacttttga    900
taatggtatg atttgtgcct cagagcagtc agtaatagtt ttagactcaa tatatgagga    960
agttaaaaaa gaatttgctt ataggggtgc ttatatatta agtaaggatg aaacagataa   1020
ggttggaaaa ataattttaa aaaatggagc cttaaatgca ggtattgtag acaacctgc    1080 ttttaaaata gcacagctgg caggagtgga tgtaccagaa aaagctaaag tacttatagg   1140
agaggtagaa tcggtagaac ttgaagaacc atttctcat gaaaagttat ctccagtttt    1200
agctatgtac agggcaagaa attttgagga tgccattgca aaaactgata aactggttag   1260
ggcaggtgga tttggacata catcttcatt gtatataaat ccaatgacag aaaaagcaaa   1320
agtagaaaaa tttagtacta tgatgaaaac atcaagaact ataattaaca caccttcatc   1380
ccaaggtggt ataggtgata tatataactt taaactagct ccttctttga cattaggctg   1440
cggttcctgg gggggaaatt ctgtatccga aaatgttggg cctaaacatt tattaaacat   1500
aaaaagtgtt gctgagagga gagaaaatat gctttggttt agagtacctg aaaaggttta   1560
tttcaaatat ggtagtcttg gagttgcatt aaaagagtta aaagttatga ataagaagaa   1620
agtatttata gtaacagata aagttcttta tcaattaggt tatgtggaca aagttacaaa   1680
agttcttgag gaactaaaaa tttcctataa ggtatttaca gatgtagaac cagatccaac   1740
ccttgctaca gctaaaaaag gtgcagcaga actgctttcc tatgaaccgg atacaattat   1800
atcagttggt ggtggttcag caatggatgc agctaagatc atgtgggtaa tgtatgagca   1860
tccagaagta aaatttgaag atttagctat gagatttatg gatataagaa agagagtata   1920
tgttttccct aagatgggag aaaaggcaat gatgatttca gtagcaacat ccgcaggaac   1980
agggtcggaa gttactccat tgcagtaat actgatgaa aaaacaggag ctaaatatcc   2040
attagctgat tatgaactaa ctccagacat ggctatagtt gatgcagaac ttatgatggg   2100
aatgccaaga ggacttacag cagcttcggg tatagatgca ttaacccatg cactggaggc   2160
gtatgtgtca ataatggcta cagaatttac caatggatta gcccttgaag cagtaaagtt   2220
gatatttgaa tatttaccaa aagcttatac agaaggtaca actaatgtaa aggcaagaga   2280
aaagatggct catgcttcat gtattgcagg tatggccttt gcaaatgcat ttttaggggt   2340
atgccactct atggcacata aattgggagc acagcatcac ataccacatg gaattgccaa   2400
tgcacttatg atagatgaag ttataaaatt caatgctgta gatgatccaa taaaacaagc   2460
tgcatttccc caatacgagt atccaaatgc taggtataga tatgctcaga tagctgattg   2520
tctgaacttg ggaggaaata cagaagagga aaaggtacaa ctattaataa atgctataga   2580
tgatttaaaa gctaagttaa atattccaga aactataaaa gaagcaggag tttcagaaga   2640
taaattctat gctactttag ataaaaatgtc agaattagct tttgatgatc agtgtacagg   2700
agctaatcca agatatccac tgataagtga aataaaacaa atgtatataa atgttttga    2760 taaaaccgaa ccaattgtag aagatgaaga aaagtaagaa aagatcaaag gatcttcttg   2820
agatcctttt tttctgcgcg taatctgctg cttgcaaaca aaaaaccac cgctaccagc   2880 ggtggtttgt ttgccggatc caccgctgag caataactag gaatgtgtgt cagttagggt   2940
ccacctaaca attcgttcaa gccgagatag ctagctagca gaagttgcag aattaagaag   3000
acaacaagga caagcaaaac attaagcatt ttgccttcct gtttttgctc acccagaaac   3060
gctggtgaaa gtaaaagatg ctgaagatca gttgggtgca cgagtgggtt acatcgaact   3120
ggatctcaac agcggtaaga tccttgagag ttttcgcccc gaagaacgtt ttccaatgat   3180
```

```
gagcactttt atcaaaaaaa tttccaataa tcccactcta agccacaaac acgccctata    3240
aaatcccgct ttaatcccac tttgagacac atgtaatatt actttacgcc ctagtatagt    3300 gataatttt tacattcaat gccacgcaaa aaataaagg ggcactataa taaagttcc       3360 ttcggaacta actaaagtaa aaaattatct ttacaacctc cccaaaaaaa agaacaggta    3420
caaagtaccc tataatacaa gcgtaaaaaa aatgagggta aaaataaaaa aataaaaaaa    3480
taaaaaaata aaaaaatata aaaataaaaa aataaaaaaa tataaaaata tttttattt     3540 aaagtttgaa aaaattttt ttatattata taatctttga agaaaagaat ataaaaatg      3600 agcctttata aaagcccatt ttttttcata tacgtaatat gacgttctaa tgttttatt    3660 ggtacttcta acattagagt aatttcttta ttttaaagc cttttctctt aagggctttt     3720 atttttttc ttaatacatt taattcctct ttttttgttg cttttccttt agcttttaat    3780
tgctcttgat aattttttt acctctaata tttctcttc tcttatattc cttttagaa       3840 attattattg tcatatattt ttgttcttct tctgtaattt ctaataactc tataagagtt    3900
tcattcttat acttatattg cttattttta tctaaataac atctttcagc acttctagtt    3960
gctcttataa cttctctttc acttaaatgt tgtctaaaca tactattaag ttctaaaaca    4020
tcatttaatg ccttctcaat gtcttctgta aagctacaaa gataatatct atataaaaat    4080
aatataagct ctctgtgtcc ttttaaatca tattctctta gttcacaaag ttttattatg    4140
tcttgtattc ttccataata taaacttctt tctctataaa tataatttat tttgcttggt    4200 ctacccttt tcctttcata tggttttaat tcaggtaaaa atccattttg tatttctctt     4260
aagtcataaa tatattcgta ctcatctaat atattgacta ctgttttga tttagagtttt   4320 atacttcctg gaactcttaa tattctcgtt gcatctaagg cttgtctatc tgctccaaag    4380
tattttaatt gattatataa atattcttga accgctttcc ataatggtaa tgctttacta    4440
ggtactgcat ttattatcca tattaaatac attcctcttc cactatctat tacatagttt    4500
ggtataggaa tactttgatt aaaataattc ttttctaagt ccattaatac ctggtcttta    4560
gttttgccag ttttataata atccaagtct ataaacagtg tatttaactc ttttatattt    4620
tctaatcgcc tacacggctt ataaaaggta tttagagtta tatagatatt ttcatcactc    4680
atatctaaat cttttaattc agcgtattta tagtgccatt ggctatatcc ttttttatct    4740
ataacgctcc tggttatcca cccttacttt ctactatgaa tattatctat atagttcttt    4800
ttattcagct ttaatgcgtt tctcacttat tcacctcccc tccctttagt aacgtgtaac    4860
tttccaaatt tacaaaagcg actcatagaa ttatttcctc ccgttaaata atagataact    4920
attaaaaata gacaatactt gctcataagt aacggtactt aaattgttta ctttggcgtg    4980
tttcattgct tgatgaaact gattttagt aaacagttga cgatattctc gattgaccca    5040
ttttgaaaca aagtacgtat atagcttcca atatttatct ggaacatctg tggtatggcg    5100
ggtaagtttt attaagacac tgtttacttt tggtttagga tgaaagcatt ccgctggcag    5160
cttaagcaat tgctgaatcg agacttgagt gtgcaagagc aaccctagtg ttcggtgaat    5220
atccaaggta cgcttgtaga atccttcttc aacaatcaga tagatgtcag acgcatggct    5280
ttcaaaaacc acttttttaa taatttgtgt gcttaaatgg taaggaatac tcccaacaat    5340 tttataccctc tgtttgttag ggaattgaaa ctgtagaata tcttggtgaa ttaaagtgac    5400
acgagtattc agttttaatt tttctgacga taagttgaat agatgactgt ctaattcaat    5460
agacgttacc tgtttactta ttttagccag tttcgtcgtt aaatgccctt tacctgttcc    5520
```

-continued

```
aatttcgtaa acggtatcgg tttcttttaa attcaattgt tttattattt ggttgagtac    5580 ttttcactc gttaaaaagt tttgagaata ttttatattt ttgttcatgt aatcactcct     5640
tcttaattac aaattttag catctaattt aacttcaatt cctattatac aaaattttaa    5700
gatactgcac tatcaacaca ctcttaagtt tgcttctaag tcttatttcc ataacttctt    5760
ttacgtttcc gggtacaatt cgtaatcatg tcatagctgt ttcctgtgtg aaattgttat    5820
ccgctcacaa ttccacacaa catacgagcc ggaagcataa agtgtaaagc ctggggtgcc    5880
taatgagtga gctaactcac attaattgcg ttgcgctcac tgcccgcttt ccagtcggga    5940
aacctgtcgt gccagaaaag gatctaggtg aagatccttt ttgataatct catgaccaaa    6000
atcccttaac gtgagttttc gttccactga gcgtcagacc ccgtagaaaa gatcaaagga    6060
tcttcttgag atcctttttt tctgcgcgta atctgctgct tgcaaacaaa aaaaccaccg    6120
ctaccagcgg tggtttgttt gccggatcaa gagctaccaa ctcttttcc gaaggtaact     6180 ggcttcagca gagcgcagat accaaatact gttcttctag tgtagccgta gttaggccac    6240
cacttcaaga actctgtagc accgcctaca tacctcgctc tgctaatcct gttaccagtg    6300
gctgctgcca gtggcgataa gtcgtgtctt accgggttgg actcaagacg atagttaccg    6360
gataaggcgc agcggtcggg ctgaacgggg ggttcgtgca cacagcccag cttggagcga    6420
acgacctaca ccgaactgag atacctacag cgtgagctat gagaaagcgc cacgcttccc    6480
gaagggagaa aggcggacag gtatccggta agcggcaggg tcggaacagg agagcgcacg    6540
agggagcttc caggggaaa cgcctggtat ctttatagtc ctgtcgggtt tcgccacctc     6600
tgacttgagc gtcgattttt gtgatgctcg tcagggggc ggagcctatg gaaaaacgcc     6660
agcaacgcgg cctttttacg gttcctggcc ttttgctggc cttttgctca catgttctttc   6720 cctgcgttat cccctgattc t                                              6741
```

<210> SEQ ID NO 9
<211> LENGTH: 6762
<212> TYPE: DNA
<213> ORGANISM: Artificial Sequence
<220> FEATURE:
<223> OTHER INFORMATION: pECPH2::AdhE2

<400> SEQUENCE: 9

```
gactagtccc gaaaagtgcc acctgttatt cctttcttga tattattcta atttcaaaca      60 aaatttata ggcattttcc gtttaaagtt taaaaattgt ggtataatta attatatcat     120
taagcggata agtgggttac acggactgct caaaattata tttggactat aggaggtctt    180
tattatgaag gtaactaagg taactaacgt tgaagaatta atgaaaaagt tagatgaagt    240
aacggctgct caaagaaat tttctagcta tactcaagaa caagtggatg aaattttcag    300
gcaggcagct atggcagcca atagtgctag aatagactta gctaaaatgg cagtggaaga    360
aagcggaatg ggaattgtag aagacaaggt cattaaaaat catttttgttg cagaatatat    420 atataacaaa tataagggtg aaaagacctg cggagttctg gaacaagatg aaggctttgg    480
tatggttaga attgcagaac ctgtaggagt tattgcagca gtagttccaa caactaatcc    540
aacatctaca gcaatattta aatcactaat agctttaaaa actagaaatg gtatagtttt    600
ttcaccacat ccaagggcaa aaaatcaac tattgcagca gctaagatag tacttgatgc    660
agcagttaaa gctggtgccc ctgaaggaat tataggctgg atagatgaac cttctattga    720
actttcacag gtggtaatga agaagcagat ctaattcctt gcaactggtg gaccaggtat    780
ggttaaggct gcctattctt caggaaagcc tgctatagga gttggtccag gtaatacacc    840
```

```
tgctgtaatt gatgaaagtg ccgacattaa aatggcagta aattcaatac tactttcaaa    900
aacttttgat aatggtatga tttgtgcttc agagcagtca gtaatagttg caagctcaat    960
atacgatgaa gtcaagaaag agtttgcaga tagaggagca tatatattaa gtaaggatga   1020
aacagataag gttggaaaaa caatcatgat taatggagct ttaaatgctg gaattgtagg   1080
gcaaagtgcc tttaaaatag ctcagatggc gggagtcagt gtaccggaag atgctaaaat   1140
acttatagga gaagttaaat cggtagaacc tgaagaagag ccctttgctc atgaaaagct   1200
gtctccagtt ctagccatgt acaaagcaaa agattttgat gaagcacttc taaaggctgg   1260
aagattagtt gaacgaggtg aatagggca tacatctgta ttgtatgtaa attcgatgac   1320
ggaaaaagta aaagtagaaa agttcagaga aactatgaag accggtagaa cattgataaa   1380
tatgccttca gcgcaaggcg ctataggaga tatatataac tttaaactag ctccttcttt   1440
gacattaggc tgtggttcct ggggaggaaa ctctgtatca gaaaatgttg gacctaaaca   1500
tttgttaaac ataaagagtg ttgctgagag gagagaaaat atgctttggt ttagagtacc   1560
tgaaaaggtt tatttcaaat atggcagcct tggagttgca ctaaaagaac tgagaattat   1620
ggagaagaaa aaggcgttta tagtaacgga taaagttctt tatcaattag gttatgtaga   1680
taaaattaca aagaacctcg atgaattaag agtttcatat aaaatattta cagatgtaga   1740
accagatcca acccttgcta cagctaaaaa aggtgcagca gaactgcttt cctatgaacc   1800
agatacaatt atagcagttg gtggtggttc ggcaatggat gctgccaaga tcatgtgggt   1860
aatgtatgag catccagaag taagatttga agatttggcc atgagattta tggatataag   1920
aaagagagta tatgtttttc ctaagatggg agaaaaggca atgatgattt cagtagcaac   1980
atccgcagga acagggtcag aagttactcc atttgcagta attacggacg aaagaacagg   2040
agctaaatat cctctggctg attatgaatt aactccaaac atggctatag ttgatgcaga   2100
acttatgatg ggaatgccaa agggctaac agcagcttca ggtatagatg cgttgactca   2160
tgcactggag gcctatgtgt caataatggc ttcagaatat accaacggat ggctcttga   2220 agcaacaaga ttagtattca aatatttgcc aatagcttat acagaaggta caattaatgt   2280
aaaggcaaga gaaaaaatgg ctcatgcttc atgtattgca ggtatggcct ttgccaatgc   2340
attttagggg gtatgccact ctatggcaca taaattggga gcacagcacc acataccaca   2400
tggaattgcc aatgcactta tgatagatga agttataaaa ttcaatgctg tagaggctcc   2460
aaggaaacaa gcggcatttc cacaatataa atatccaaat gttaaaagaa gatatgctag   2520
aatagctgat tacctaaatt taggtggaag tacagatgat gaaaaagtac aattgctaat   2580
aaatgctata gatgacttaa aaactaagtt aaatattcca aagactatta agaagcagg   2640 agtttcagaa gataaattct atgctacttt agatacaatg tcagaactgg cttttgatga   2700
tcaatgtaca ggagctaatc cacgatatcc actaatagga gaaataaaac aaatgtatat   2760
aaatgcattt gatacaccaa aggcaactgt ggagaagaaa acaagaaaga aaagtaaga   2820 aaagatcaaa ggatcttctt gagatccttt ttttctgcgc gtaatctgct gcttgcaaac   2880
aaaaaaacca ccgctaccag cggtggtttg tttgccggat ccaccgctga gcaataacta   2940
ggaatgtgtg tcagttaggg tccacctaac aattcgttca agccgagata gctagctagc   3000
agaagttgca gaattaagaa gacaacaagg acaagcaaaa cattaagcat tttgccttcc   3060 tgttttgct cacccagaaa cgctggtgaa agtaaaagat gctgaagatc agttgggtgc   3120
acgagtgggt tacatcgaac tggatctcaa cagcggtaag atccttgaga gttttcgccc   3180
```

```
cgaagaacgt tttccaatga tgagcacttt tatcaaaaaa atttccaata atcccactct    3240
aagccacaaa cacgccctat aaaatcccgc tttaatccca ctttgagaca catgtaatat    3300
tactttacgc cctagtatag tgataatttt ttacattcaa tgccacgcaa aaaataaag    3360 gggcactata ataaaagttc cttcggaact aactaaagta aaaaattatc tttacaacct    3420 cccaaaaaa aagaacaggt acaaagtacc ctataataca agcgtaaaaa aaatgagggt    3480
aaaaataaaa aaataaaaaa ataaaaaaat aaaaaaatat aaaaataaaa aaataaaaaa    3540
atataaaaat attttttatt taaagtttga aaaaaatttt tttatattat ataatctttg    3600
aagaaaagaa tataaaaaat gagcctttat aaaagcccat ttttttttcat atacgtaata    3660 tgacgttcta atgttttat tggtacttct aacattagag taatttcttt attttaaag    3720 ccttttctt taagggcttt tattttttt cttaatacat ttaattcctc ttttttgtt    3780 gcttttcctt tagcttttaa ttgctcttga taatttttt tacctctaat attttctctt    3840
ctcttatatt cctttttaga aattattatt gtcatatatt tttgttcttc ttctgtaatt    3900
tctaataact ctataagagt ttcattctta tacttatatt gcttattttt atctaaataa    3960
catctttcag cacttctagt tgctcttata acttctcttt cacttaaatg ttgtctaaac    4020
atactattaa gttctaaaac atcatttaat gccttctcaa tgtcttctgt aaagctacaa    4080
agataatatc tatataaaaa taatataagc tctctgtgtc cttttaaatc atattctctt    4140
agttcacaaa gttttattat gtcttgtatt cttccataat ataaacttct ttctctataa    4200
atataattta ttttgcttgg tctacccttt ttccttttcat atggttttaa ttcaggtaaa    4260
aatccatttt gtatttctct taagtcataa atatattcgt actcatctaa tatattgact    4320 actgttttttg atttagagtt tatacttcct ggaactctta atattctcgt tgcatctaag    4380
gcttgtctat ctgctccaaa gtattttaat tgattatata atatattcttg aaccgctttc    4440 cataatggta atgctttact aggtactgca tttattatcc atattaaata cattcctctt    4500
ccactatcta ttcatagtt tggtatagga atactttgat taaataatt cttttctaag    4560 tccattaata cctggtcttt agttttgcca gttttataat aatccaagtc tataaacagt    4620
gtatttaact ctttatattt ttctaatcgc ctacacggct tataaaaggt atttagagtt    4680
atatagatat tttcatcact catatctaaa tcttttaatt cagcgtattt atagtgccat    4740
tggctatatc ctttttttatc tataacgctc ctggttatcc acccttact tctactatga    4800 atattatcta tatagttctt tttattcagc tttaatgcgt ttctcactta ttcacctccc    4860 ctcccttag taacgtgtaa cttttccaaat ttacaaagc gactcataga attatttcct    4920
cccgttaaat aatagataac tattaaaaat agacaatact tgctcataag taacggtact    4980
taaattgttt actttggcgt gtttcattgc ttgatgaaac tgattttag taaacagttg    5040 acgatattct cgattgaccc atttgaaac aaagtacgta tatagcttcc aatatttatc    5100
tggaacatct gtggtatggc gggtaagttt tattaagaca ctgtttactt ttggtttagg    5160
atgaaagcat tccgctggca gcttaagcaa ttgctgaatc gagacttgag tgtgcaagag    5220
caaccctagt gttcggtgaa tatccaaggt acgcttgtag aatccttctt caacaatcag    5280
atagatgtca gacgcatggc tttcaaaaac cacttttta ataatttgtg tgcttaaatg    5340
gtaaggaata ctcccaacaa ttttataccct ctgtttgtta gggaattgaa actgtagaat    5400
atcttggtga attaaagtga cacgagtatt cagttttaat ttttctgacg ataagttgaa    5460
tagatgactg tctaattcaa tagacgttac ctgtttactt attttagcca gtttcgtcgt    5520
taaatgccct ttacctgttc caatttcgta aacggtatcg gtttcttta aattcaattg    5580
```

```
ttttattatt tggttgagta cttttcact cgttaaaaag ttttgagaat attttatatt      5640
tttgttcatg taatcactcc ttcttaatta caaatttta gcatctaatt taacttcaat       5700
tcctattata caaatttta agatactgca ctatcaacac actcttaagt ttgcttctaa       5760
gtcttatttc cataacttct tttacgtttc cgggtacaat tcgtaatcat gtcatagctg      5820
tttcctgtgt gaaattgtta tccgctcaca attccacaca acatacgagc cggaagcata     5880
aagtgtaaag cctggggtgc ctaatgagtg agctaactca cattaattgc gttgcgctca      5940
ctgcccgctt tccagtcggg aaacctgtcg tgccagaaaa ggatctaggt gaagatcctt     6000
tttgataatc tcatgaccaa aatcccttaa cgtgagtttt cgttccactg agcgtcagac      6060
cccgtagaaa agatcaaagg atcttcttga gatccttttt ttctgcgcgt aatctgctgc     6120
ttgcaaacaa aaaaccacc gctaccagcg gtggtttgtt tgccggatca agagctacca      6180
actctttttc cgaaggtaac tggcttcagc agagcgcaga taccaaatac tgttcttcta     6240
gtgtagccgt agttaggcca ccacttcaag aactctgtag caccgcctac atacctcgct      6300
ctgctaatcc tgttaccagt ggctgctgcc agtggcgata agtcgtgtct taccgggttg    6360
gactcaagac gatagttacc ggataaggcg cagcggtcgg gctgaacggg gggttcgtgc     6420
acacagccca gcttggagcg aacgacctac accgaactga gatacctaca gcgtgagcta     6480
tgagaaagcg ccacgcttcc cgaagggaga aaggcggaca ggtatccggt aagcggcagg     6540
gtcggaacag gagagcgcac gagggagctt ccaggggaa acgcctggta tctttatagt      6600
cctgtcgggt ttcgccacct ctgacttgag cgtcgatttt tgtgatgctc gtcaggggg     6660 cggagcctat ggaaaaacgc cagcaacgcg gcctttttac ggttcctggc cttttgctgg    6720
ccttttgctc acatgttctt tcctgcgtta tcccctgatt ct                        6762
```